(12) United States Patent
Saitou et al.

(10) Patent No.: US 8,668,636 B2
(45) Date of Patent: Mar. 11, 2014

(54) ELECTRONIC ENDOSCOPE SYSTEM, PROCESSOR FOR ELECTRONIC ENDOSCOPE, AND METHOD OF DISPLAYING VASCULAR INFORMATION

(75) Inventors: Takaaki Saitou, Kanagawa (JP); Yasuhiro Minetoma, Kanagawa (JP); Minkyung Chun, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 669 days.

(21) Appl. No.: 12/923,335

(22) Filed: Sep. 15, 2010

(65) Prior Publication Data

US 2011/0077462 A1 Mar. 31, 2011

(30) Foreign Application Priority Data

Sep. 30, 2009 (JP) ................. 2009-227549
Sep. 30, 2009 (JP) ................. 2009-228771
Mar. 26, 2010 (JP) ................. 2010-072066

(51) Int. Cl.
*A61B 1/04* (2006.01)
*A61B 1/00* (2006.01)
*A61B 1/06* (2006.01)

(52) U.S. Cl.
USPC ..................... 600/109; 600/118; 600/180

(58) Field of Classification Search
USPC ......... 600/109, 126, 473, 475, 410, 476, 477, 600/323, 118, 178
See application file for complete search history.

(56) References Cited

U.S. PATENT DOCUMENTS

| | | | |
|---|---|---|---|
| 4,878,113 A | 10/1989 | Nakamura | |
| 4,998,973 A | 3/1991 | Kikuchi | |
| 5,001,556 A * | 3/1991 | Nakamura et al. | 348/70 |
| 5,512,940 A * | 4/1996 | Takasugi et al. | 348/71 |
| 6,556,853 B1 * | 4/2003 | Cabib et al. | 600/407 |
| 7,043,287 B1 * | 5/2006 | Khalil et al. | 600/310 |
| 7,667,180 B2 * | 2/2010 | Maeda | 250/208.1 |
| 7,767,980 B2 * | 8/2010 | Yamaguchi et al. | 250/458.1 |

(Continued)

FOREIGN PATENT DOCUMENTS

| EP | 2070469 | 6/2009 |
|---|---|---|
| EP | 2105090 A1 | 9/2009 |

(Continued)

OTHER PUBLICATIONS

Office Action, issued by the European Patent Office (EPO) on Oct. 15, 2013 in connection with European Patent Application No. 10178592.1.

*Primary Examiner* — Philip R Smith
*Assistant Examiner* — William Chou
(74) *Attorney, Agent, or Firm* — Jean C. Edwards; Edwards Neils PLLC

(57) ABSTRACT

Illumination light projected into a body cavity includes first to third narrowband rays of different wavelength ranges, at least one of these narrowband rays has a central wavelength of not more than 450 nm. Under these narrowband rays, first to third narrowband image signals are respectively obtained through an endoscope. Based on the first to third narrowband image signals, vascular areas containing blood vessels are determined, and a first luminance ratio between the first and third narrowband signals and a second luminance ratio between the second and third narrowband signals are calculated at every pixel of the vascular areas. From the calculated first and second luminance ratios, information about both the depth and oxygen saturation of the blood vessels is acquired with reference to correlation data that correlates the first and second luminance ratios to the vessel depth and the oxygen saturation.

11 Claims, 28 Drawing Sheets

(56) References Cited

U.S. PATENT DOCUMENTS

| | | | |
|---|---|---|---|
| 7,873,407 B2* | 1/2011 | Levenson et al. | 600/476 |
| 8,260,016 B2* | 9/2012 | Maeda et al. | 382/128 |
| 8,301,229 B2* | 10/2012 | Gono et al. | 600/473 |
| 2005/0251049 A1* | 11/2005 | Cane et al. | 600/476 |
| 2006/0184037 A1 | 8/2006 | Ince et al. | |
| 2006/0276966 A1* | 12/2006 | Cotton et al. | 702/1 |
| 2007/0043341 A1* | 2/2007 | Anderson et al. | 606/12 |
| 2008/0294105 A1* | 11/2008 | Gono et al. | 604/109 |
| 2009/0247881 A1* | 10/2009 | Maeda et al. | 600/476 |

FOREIGN PATENT DOCUMENTS

| | | |
|---|---|---|
| JP | 2648494 | 5/1997 |
| JP | 2761238 | 3/1998 |
| JP | 3559755 | 5/2004 |

* cited by examiner

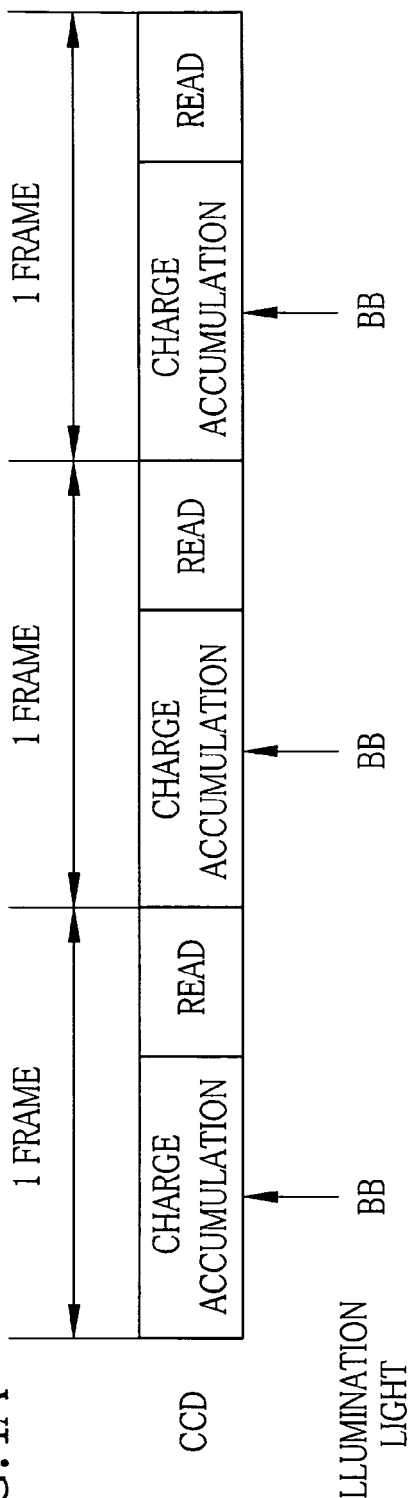
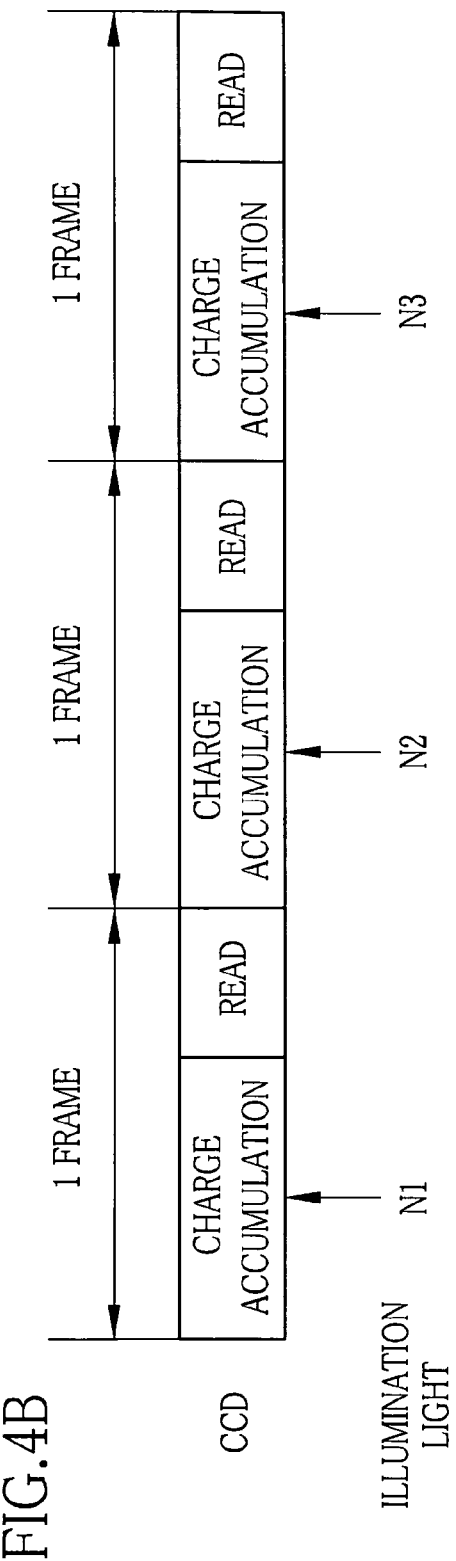

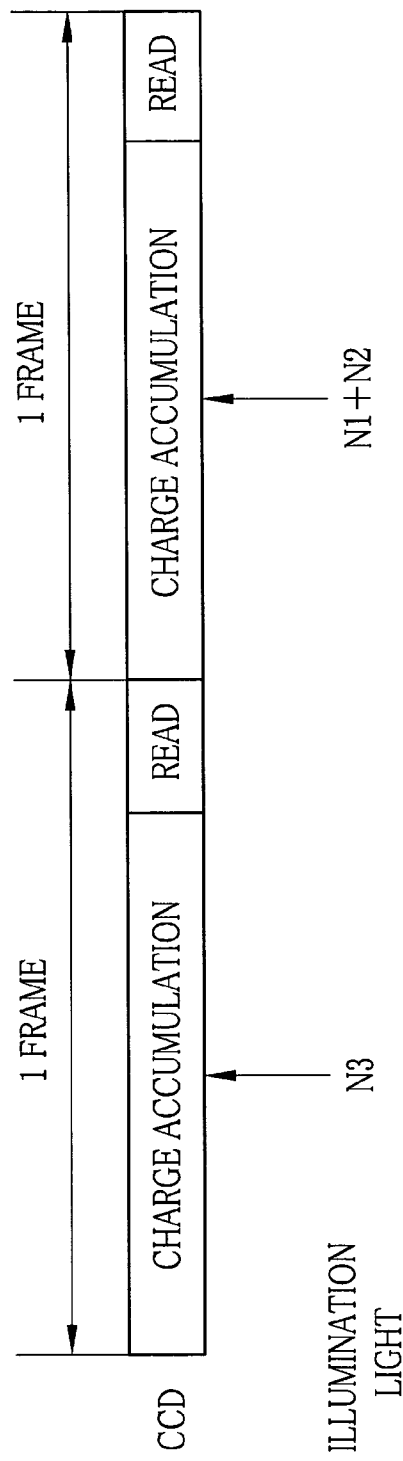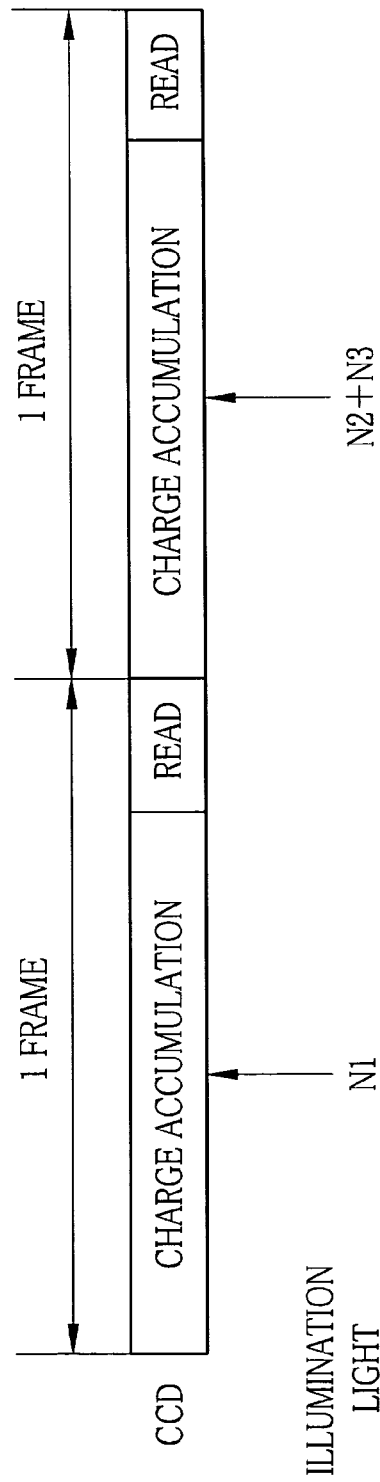

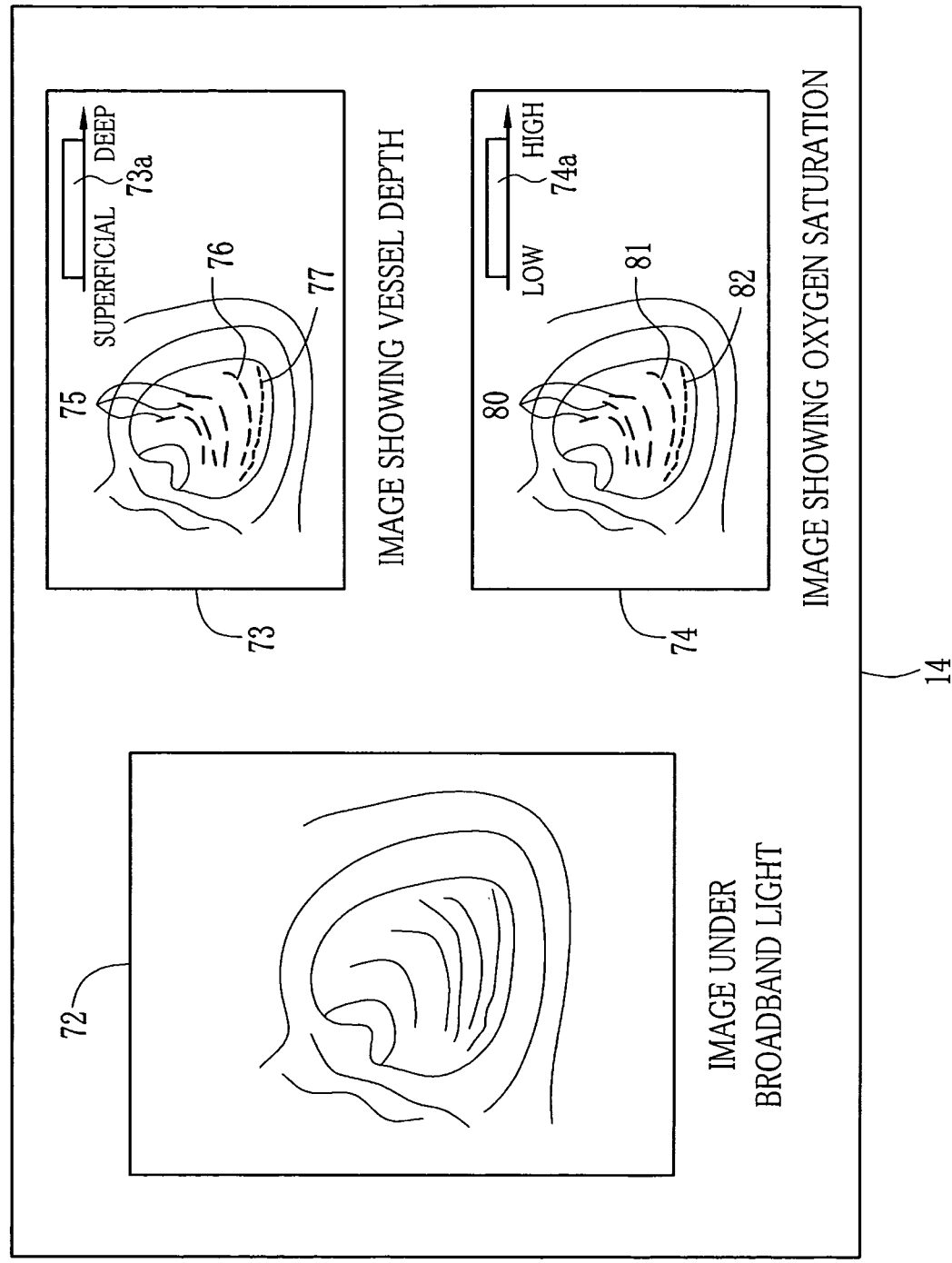

ELECTRONIC ENDOSCOPE SYSTEM, PROCESSOR FOR ELECTRONIC ENDOSCOPE, AND METHOD OF DISPLAYING VASCULAR INFORMATION

FIELD OF THE INVENTION

The present invention relates to an electronic endoscope system that acquires vascular information about blood vessels from images captured through an endoscope. The present invention also relates to a processor for the electronic endoscope, and a method of displaying the vascular information.

CROSS-REFERENCE TO RELATED APPLICATIONS

The present application claims priority from Japanese Patent Application Nos. 2009-227549, filed Sep. 30, 2009, 2009-228771, filed Sep. 30, 2009, and 2010-072066, filed Mar. 26, 2010, the contents of all of which are herein incorporated by reference in their entirety.

BACKGROUND OF THE INVENTION

In recent medical field, electronic endoscopes are frequently used for diagnoses and treatment. The electronic endoscope has a probing portion that is inserted into a body cavity, such as stomach, of a subject under inspection, and an imaging unit including a CCD or the like is incorporated in a distal end of the probing portion. The electronic endoscope is also connected to a light source unit, so that light from the light source unit is projected from the distal end of the probing portion to illuminate the inside of the body cavity. While the inside of the body cavity is illuminated, subject tissues inside the body cavity are imaged by the imaging unit. Captured images are processed in various ways in a processor, which is also connected to the electronic endoscope, and the processed images are displayed on a monitor. The electronic endoscope thus allows viewing images of the inside of the body cavity of the subject under inspection in real time fashion, enabling the doctor to make exact diagnoses.

The light source unit generally uses a white light source, such as a xenon lamp that emits white light having a broadband wavelength range from the blue ray region to the red ray region. Using the white broadband light for illuminating the body cavity allows capturing such an image that is useful for observing the whole subject tissues inside the cavity. However, the image captured under the broadband light is indeed effective for rough perception of the subject tissues, but insufficient for observing the details of capillaries or microscopic vessels, deep blood vessels, bit-patterns (gland orifice structure), and surface asperity of the subject tissues, such as concaves and convexes. It is known in the art that the details of the subject tissues will be more visible when illuminated with narrowband light having a limited wavelength range. It is also known in the art that various kinds of information about the subject tissues, such as arterial and venous oxygen saturation levels, may be acquired from image data obtained under the narrowband illumination light, and the acquired information may be graphically displayed.

For example, Japanese Patent No. 3559755 discloses projecting sequentially three kinds of narrowband rays: the red ray, the green ray and the blue ray, to capture an image during each projection period of the ray of one kind. Because the ray of longer wavelength can reach deeper inside the tissues, and the wavelengths of the blue, green and red rays get longer in this order, an image of superficial blood vessels may be obtained during the blue ray illumination, an image of middle-layer vessels may be obtained during the green ray illumination, and an image containing enhanced deep blood vessels may be obtained during the red ray illumination. This prior art also discloses processing the respective images obtained during the separated color illumination, to produce an image showing the superficial blood vessels, the middle-layer vessels, and the deep blood vessels in different colors from each other.

Japanese Patent No. 2648494 discloses projecting three kinds of narrowband infrared rays IR1, IR2 and IR3, wherein the rays IR1 and IR3 are of such infrared regions that the light absorbance of blood vessels to the rays IR1 and IR3 will change according to the change in oxygen saturation of blood, whereas the ray IR2 is of such an infrared region that the light absorbance of blood vessels to the ray IR2 will not change regardless of oxygen saturation of blood. An image is captured during each projection period of the ray of one kind. On the basis of images captured under the illumination of the narrowband rays IR1 and IR3, to which the light absorbance of the blood vessels changes with the oxygen saturation, and an image captured under the illumination of the narrowband light IR2, to which the light absorbance will not change, variations in luminance between these images are calculated. The calculated luminance variations are reflected in an image to show the variations as gray-gradations or artificial color variations, so the image provides information about the oxygen saturation in the blood vessels.

In Japanese Patent No. 2761238, an endoscope captures one image while projecting a narrowband ray of a wavelength range around 650 nm, to which the light absorbance of the vessels will change according to the change in oxygen saturation, and other images while projecting a narrowband ray of a wavelength range around 569 nm light and a narrowband ray of a wavelength range around 800 nm, to which the light absorbance of the vessels will not change regardless of the oxygen saturation. Base on these images, information on the distribution of the hemoglobin amount and information on the oxygen saturation are simultaneously acquired, to produce a color image reflecting these two kinds of information.

There has recently been a demand for such a technology that makes the depth and oxygen saturation of the blood vessels perceivable at the same time on making diagnoses, treatments or the like. However, acquiring information about the blood vessel depth and the oxygen saturation at the same time has been difficult because of many factors, for example, because the light absorbance of hemoglobin in the blood vessels obviously changes depending on the wavelength (see FIG. 3), although simultaneous detection of the hemoglobin amount and the oxygen saturation can be achieved using illumination rays of different narrowband ranges, as disclosed in the above-mentioned Japanese Patent No. 2761238.

Projecting the three narrowband rays of red, green and blue, like in Japanese Patent No. 3559755, may provide information about the blood vessel depth, but cannot provide information about the oxygen saturation. On the other hand, projecting the narrowband infrared rays IR1, IR2 and IR3, like in Japanese Patent No. 2648494, may provide information about the oxygen saturation, but cannot provide information about the blood vessel depth. Even with those rays of wavelength regions which meet both conditions defined in the Japanese Patents Nos. 3559755 and 2648494, it is hard to acquire information about the blood vessel depth and information about the oxygen saturation at once.

The present invention is provided in view of the foregoing problem, and has an object to provide an electronic endoscope system and a processor for an endoscope, which allow acquiring information about the blood vessel depth and information about the oxygen saturation as well. The present invention also has an object to provide a method of displaying these two kinds of vascular information at the same time.

SUMMARY OF THE INVENTION

The present invention provides an electronic endoscope system that comprises an illuminating device for projecting illumination light toward subject tissues inside a body cavity, including blood vessels; an electronic endoscope having an imaging device for capturing and outputting image signals that represent luminance of the illumination light as being projected toward and then reflected from the subject tissues; a first narrowband signal obtaining device for obtaining first and second narrowband signals from the image signals; and a vascular information acquiring device for acquiring vascular information about the blood vessels on the basis of the first and second narrowband signals.

The illumination light includes first and second narrowband rays of different wavelength ranges from each other, or has a wavelength range including both of the wavelength ranges of the first and second narrowband rays. At least one of the first and second narrowband rays has a central wavelength of not more than 450 nm. The first and second narrowband signals correspond to the first and second narrowband rays respectively. The vascular information includes both information about vessel depth and information about oxygen saturation representative of the percentage of oxygenated hemoglobin in the blood vessels. For example, the central wavelengths of the first and second narrowband rays may be 445 nm and 473 nm, 405 nm and 445 nm, or 405 nm and 473 nm, respectively, or may have other values.

The first and second narrowband rays preferably include such wavelengths, at which light absorbance in oxygenated hemoglobin differs from light absorbance in reduced hemoglobin that is not combined with oxygen, and that the light absorbance in hemoglobin to the first narrowband ray and the light absorbance in hemoglobin to the second narrowband ray differ from each other.

Preferably, the electronic endoscope system of the present invention further comprises a second narrowband signal obtaining device for obtaining a third narrowband signal from the imaging signals, the third narrowband signal corresponding to a third narrowband ray having a different wavelength range from the first and second narrowband rays; a luminance ratio calculator for calculating a first luminance ratio between the first and third narrowband signals and a second luminance ratio between the second and third narrowband signals; and a first storage device previously storing correlations between the first and second luminance ratios and the vessel depth and the oxygen saturation. For example, the vascular information acquiring device may acquire the information about the vessel depth and the information about the oxygen saturation from the first and second luminance ratios calculated by the luminance ratio calculator, with reference to the correlation stored in the first storage device.

The first storage device preferably stores the correlation by correlating a luminance coordinate system that indicates the first and second luminance ratios to a vascular information coordinate system that indicates the vessel depth and the oxygen saturation. The vascular information acquiring device may determine first coordinates in the luminance coordinate system, corresponding to the first and second luminance ratios calculated by the luminance ratio calculator. Then the vascular information acquiring device may determine second coordinates in the vascular information coordinate system, corresponding to the first coordinates of the luminance coordinate system, one coordinate value of the second coordinates representing the vessel depth and the other coordinate value of the second coordinates representing the oxygen saturation.

In an embodiment, the first narrowband ray has a wavelength range of 440±10 nm, the second narrowband ray has a wavelength range of 470±10 nm, and the third narrowband ray has a wavelength range of 400±10 nm. However, the present invention is not limited to this embodiment. For example, the first narrowband ray may have the wavelength range of 400±10 nm, the second narrowband ray may have the wavelength range of 440±10 nm, and the third narrowband ray may have the wavelength range of 470±10 nm, or the first narrowband ray may have the wavelength range of 470±10 nm, the second narrowband ray may have the wavelength range of 400±10 nm, and the third narrowband ray may have the wavelength range of 440±10 nm.

In an embodiment where the imaging device has red pixels, green pixels and blue pixels, which are provided with red, green and blue filters respectively, the illuminating device is capable of projecting white broadband light having a wavelength range covering red, green and blue regions, to which the red, green and blue pixels are respectively sensitive. In this embodiment, the electronic endoscope system may preferably comprise an ordinary image producer for producing an ordinary image from the image signal as captured while the broadband light is being projected.

Preferably, two of the first to third narrowband rays have wavelength ranges, to which either the blue pixel or the green pixel is sensitive, whereas a remaining one of the first to third narrowband rays has a wavelength range, to which both the blue pixel and the green pixel are sensitive.

In an embodiment, the illuminating device is capable of projecting the first to third narrowband rays individually, wherein the narrowband signal obtaining device may obtain the first to third narrowband signals respectively from three frames of the image signals, which are captured respectively under the first to third narrowband rays which are sequentially projected from the illuminating device.

In another embodiment, the illuminating device is capable of projecting the first to third narrowband rays individually, and the narrowband signal obtaining device obtains the first to third narrowband signal from first and second frames of the image signals. The first frame may be captured while the illuminating device is projecting one of the first to third narrowband rays that has a wavelength range, to which either the blue pixel or the green pixel is sensitive. On the other hand, the second frame may be captured while the illuminating device is projecting other two of the first to third narrowband rays simultaneously.

Preferably, the electronic endoscope system further comprises a second storage device storing correlation between luminance values of blue and green pixels contained in a frame of the image signals, which is captured under the broadband light. In this embodiment, the illuminating device is capable of projecting the broadband light and at least one of the first to third narrowband rays simultaneously, and the imaging device captures a first frame while the illuminating device is projecting one of the first to third narrowband rays that has a wavelength range, to which either the blue pixel or the green pixel is sensitive, simultaneously with the broadband light. The imaging device captures a second frame while the illuminating device is projecting other two of the first to third narrowband rays simultaneously with the broadband light. With reference to the correlation stored in the second storage device, the narrowband signal obtaining device obtains the first to third narrowband signals by subtracting those luminance values which are based on the broadband light from respective luminance values of the first and second frames.

In another embodiment, the illuminating device is capable of projecting white broadband light having a wavelength range covering from blue region to red region as well as all the wavelength ranges of the first to third narrowband rays. In this embodiment, the broadband light as reflected from the subject tissues is filtered through an optical filter, to selectively pass one of the first to third narrowband rays to the imaging device, so the imaging device sequentially outputs image signals each corresponding to the one of the first to third narrowband rays that passes through the optical filter. Then, the narrowband signal obtaining device may obtain these image signals as the first to third narrowband signals.

Preferably, the electronic endoscope system further comprises a third narrowband signal obtaining device for obtaining a fourth narrowband signal corresponding to a fourth narrowband ray that has a different wavelength range from the first to third narrowband rays. In this example, the vascular information acquiring device acquires the vascular information including information about both the vessel depth and the oxygen saturation on the basis of the first to fourth narrowband signals.

It is also possible to obtain multiple narrowband signals corresponding to other narrowband rays of different wavelength ranges from the first to third narrowband rays, and acquire the information about the vessel depth and the oxygen saturation on the basis of the multiple narrowband signals and the first to third narrowband signals as well.

The electronic endoscope system of the present invention preferably comprises a display device for displaying the information on the vessel depth and the information on the oxygen saturation selectively from one another or simultaneously with each other.

In another aspect of the present invention, a processor for an electronic endoscope is provided. The electronic endoscope projects illumination light toward subject tissues inside a body cavity and outputs image signals representative of luminance of the illumination light as being reflected from the subject tissues and captured through an imaging device. The illumination light includes first and second narrowband rays of different wavelength ranges from each other, at least one of the first and second narrowband rays having a central wavelength of not more than 450 nm, or the illumination light has a wavelength range including both of the wavelength ranges of the first and second narrowband rays. The processor according to the present invention comprises a signal receiving device for receiving the image signals from the electronic endoscope; a narrowband signal obtaining device for obtaining first and second narrowband signals from the image signals, the first and second narrowband signals respectively corresponding to the first and second narrowband rays; and a vascular information acquiring device for acquiring vascular information about the blood vessels on the basis of the first and second narrowband signals, wherein the vascular information include both information about the vessel depth and information about the oxygen saturation.

The present invention also provides a method of acquiring vascular information, which comprises the steps of projecting illumination light through an electronic endoscope toward subject tissues inside a body cavity that include blood vessels; capturing and outputting image signals through an imaging device, the imaging signal representing luminance of the illumination light as being reflected from the subject tissues; obtaining first and second narrowband signals from the image signals; and acquiring vascular information about the blood vessels on the basis of the first and second narrowband signals, wherein the first and second narrowband signals correspond respectively to first and second narrowband rays of different wavelength ranges from each other, at least one of the first and second narrowband rays has a central wavelength of not more than 450 nm, and the illumination light includes the first and second narrowband rays or has a wavelength range including both of the wavelength ranges of the first and second narrowband rays, so that the acquired vascular information includes both information about the vessel depth and information about the oxygen saturation.

According to the present invention, the vascular information is acquired on the basis of the first and second narrowband signals that correspond respectively to the first and second narrowband rays of different wavelength ranges from each other, at least one of which has a central wavelength of not more than 450 nm. Thus, the acquired vascular information may include both information about the vessel depth and information about the oxygen saturation.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 4A is an explanatory diagram illustrating an imaging operation of a CCD in an ordinary lighting imaging mode;

FIG. 4B is an explanatory diagram illustrating an imaging operation of the CCD in a special lighting imaging mode;

FIG. 11 is an explanatory diagram illustrating an imaging operation in a second embodiment of the present invention;

FIG. 12 is an explanatory diagram illustrating a variation of the imaging operation in the second embodiment of the present invention;

FIG. 21 is a diagram illustrating a monitor screen displaying an image showing information on the vessel depth and an image showing information on the oxygen saturation, wherein color bar scales are shown in the respective images;

DESCRIPTION OF THE PREFERRED EMBODIMENTS

Figure 1:
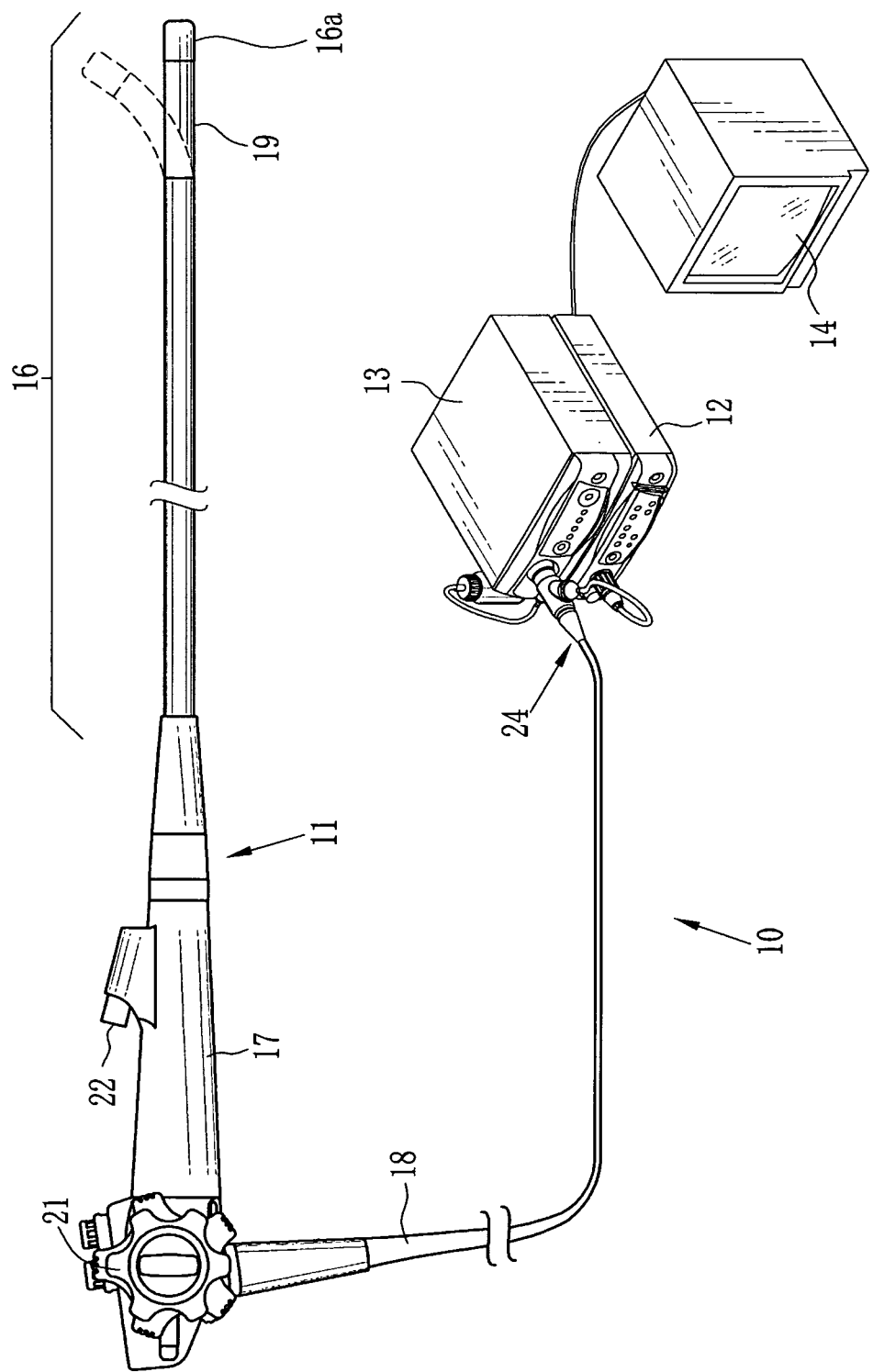
FIG. 1 is a diagram illustrating an outer appearance of an electronic endoscope system according to a first embodiment of is the present invention.

As shown in FIG. 1, an electronic endoscope system 10 according to the first embodiment of the present invention includes an electronic endoscope 11, a processor 12, a light source unit 13 and a monitor 14. The endoscope 11 images the interior of a body cavity of a subject under inspection. The processor 12 produces images of the tissues inside the body cavity from electronic signals from the endoscope 11. The light source unit 13 provides light for illuminating the inside of the body cavity, and the monitor 14 displays the images of the interior of the body cavity. The electronic endoscope 11 includes a flexible probing portion 16 to be inserted into the body cavity, a handling portion 17 coupled to a proximal end of the probing portion 16, and a cord 18 connecting the handling portion 17 to the processor 12 and the light source unit 13.

The probing portion 16 has a curving distal end that consists of serially linked segments. The curving portion 19 may curve in any directions in response to the operation on an angle knob 21 of the handling portion 17. A tip portion 16a formed in the distal end of the curving portion 19 contains an optical system for imaging the interior of the body cavity. The tip portion 16a may be oriented to any desirable direction inside the body cavity through the curving portion 19.

The cord 18 is coupled to a connector 24 on the side of the processor 12 and the light source unit 13. The connector 24 is a complex connector consisting of a connector terminal for data communication and a connector terminal for light source. Through this connector 24, the electronic endoscope 11 may be removably connected to the processor 12 and the light source unit 13.

Figure 2:
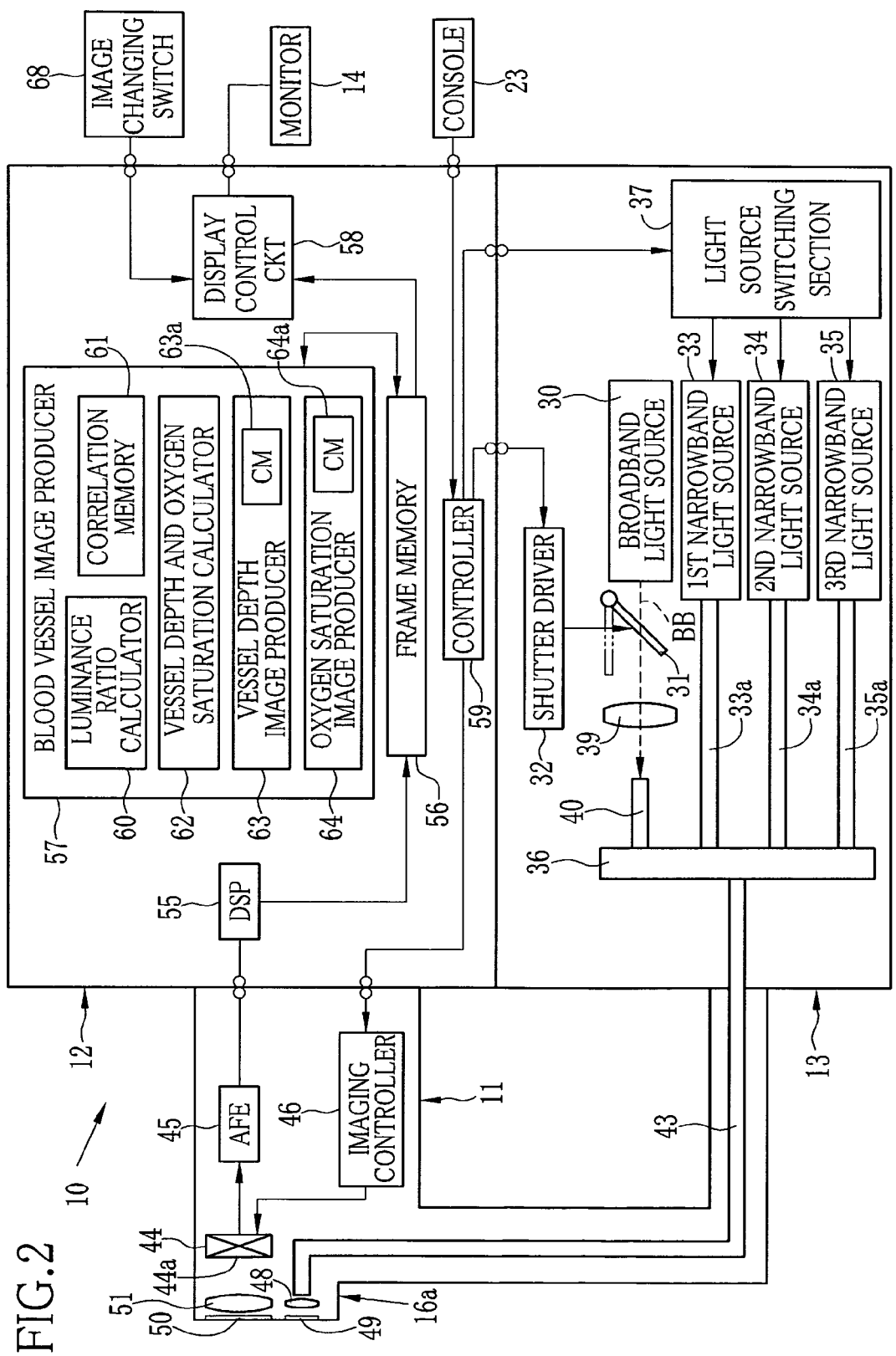
FIG. 2 is a block diagram illustrating a circuitry of the electronic endoscope system of the first embodiment.

As shown in FIG. 2, the light source unit 13 includes a broadband light source 30, a shutter 31, a shutter driver 32, first to third narrowband light sources 33 to 35, a photocoupler 36, and a light source switching section 37. The broadband light source 30 may be a xenon lamp, white LED or micro-white light source, which emits broadband light BB having a wavelength range from the red ray region to the blue ray region (about 470 nm to 700 nm). The broadband light source 30 is kept ON while the electronic endoscope 11 is in operation. The broadband light BB from the broadband light source 30 is converged through a condenser lens 39 and then introduced into a broadband optical fiber 40.

A shutter 31 is installed in between the broadband light source 30 and the condenser lens 39, so as to be movable into a light path of the broadband light BB to block the broadband light BB, or out of the light path to allow the broadband light BB to travel to the condenser lens 39. A shutter driver 32, which is connected to a controller 59 that is included in the processor 12, controls driving the shutter 31 according to instructions from the controller 59.

The first to third narrowband light sources 33 to 35 may be laser diodes or the like. The first narrowband light source 33 emits a first narrowband ray N1, the second narrowband light source 34 emits a second narrowband ray N2, and the third narrowband light source 35 emits a third narrowband ray N3. For example, the first narrowband ray N1 has a wavelength limited to 440±10 nm, preferably to 445 nm, the second narrowband ray N2 has a wavelength limited to 470±10 nm, preferably to 473 nm, and the third narrowband ray N3 has a wavelength limited to 400±10 nm, preferably to 405 nm. The first to third narrowband light sources 33 to 35 are connected to the first to third narrowband optical fibers 33a to 35a respectively, so that the first to third narrowband rays N1 to N3 from the respective light sources are introduced into the first to third narrowband optical fibers 33a to 35a.

The coupler 36 couples the broadband optical fiber 40 and the first to third narrowband optical fibers 33a to 35a to a light guide 43 in the electronic endoscope. Thus, the broadband light BB can enter the light guide 43 via the broadband optical fiber 40. On the other hand, the first to third narrowband rays N1 to N3 can enter the light guide 43 via the first to third narrowband optical fibers 33a to 35a respectively.

The light source switching section 37 is connected to the controller 59 in the processor 12, to turn the first to third narrowband light sources 33 to 35 ON or OFF according to the instruction from the controller 59. In the first embodiment, when the system 10 is set at an ordinary lighting imaging mode, the broadband light source 30 is turned ON to illuminate the inside of body cavity with the broadband light BB to capture an image under ordinary lighting, whereas the first to third narrowband light sources 33 to 35 are turned OFF. On the other hand, when the system 10 is set at a special lighting imaging mode using the first to third narrowband rays N1 to N3, the broadband light BB stops being projected into the body cavity, and the first to third narrowband light sources 33 to 35 are sequentially turned ON and OFF to illuminate the body cavity sequentially with the first to third narrowband rays N1 to N3, thereby to capture images under special lighting.

Specifically, the first narrowband light source 33 is first turned on through the light source switching section 37. Then, while the first narrowband ray N1 is illuminating inside the body cavity, imaging of the subject tissues is carried out. When the imaging is complete, the controller 59 outputs an instruction to switch over the light source, upon which the first narrowband light source 33 is turned OFF, and the second narrowband light source 34 is turned ON. Thereafter when an image has been captured while the second narrowband ray N2 is illuminating the body cavity, the second narrowband light source 34 is turned OFF, and the third narrowband light source 35 is turned ON. Moreover, when another image has been captured while the third narrowband ray N3 is illuminating the body cavity, the third narrowband light source 35 is turned OFF.

The electronic endoscope 11 includes the light guide 43, a CCD 44, an analog front end (AFE) 45, and an imaging controller 46. The light guide 43 may be a large-diameter optical fiber or a handle fiber, which has an inlet end inserted into the coupler 36 in the light source unit 13. An outlet end of the light guide 43 is opposed to a projection lens 48 that is mounted in the tip portion 16a. The light from the light source unit 13 is conducted through the light guide 43 and then outputs to the projection lens 48. The light entering the projection lens 48 is projected into the body cavity through a lightening window 49 that is mounted in a face end of the tip portion 16a. The broadband light BB and the first to third narrowband rays N1 to N3 are each reflected from the body cavity, and then fall on a condenser lens 51 through an observation window 50 that is mounted in the face end of the tip portion 16a.

The CCD 44 receives the light from the condenser lens 51 on a photo sensing surface 44a to convert the received light amount to electric charges and accumulate the charges. The accumulated charges are read out as image signals and sent to the AFE 45. The CCD 44 is a color CCD having three-color pixels arranged on the photo sensing surface 44a, wherein filters for red (R), green (G) and blue (B) are respectively allocated to the pixels for red (R), green (G) and blue (B).

Figure 3:
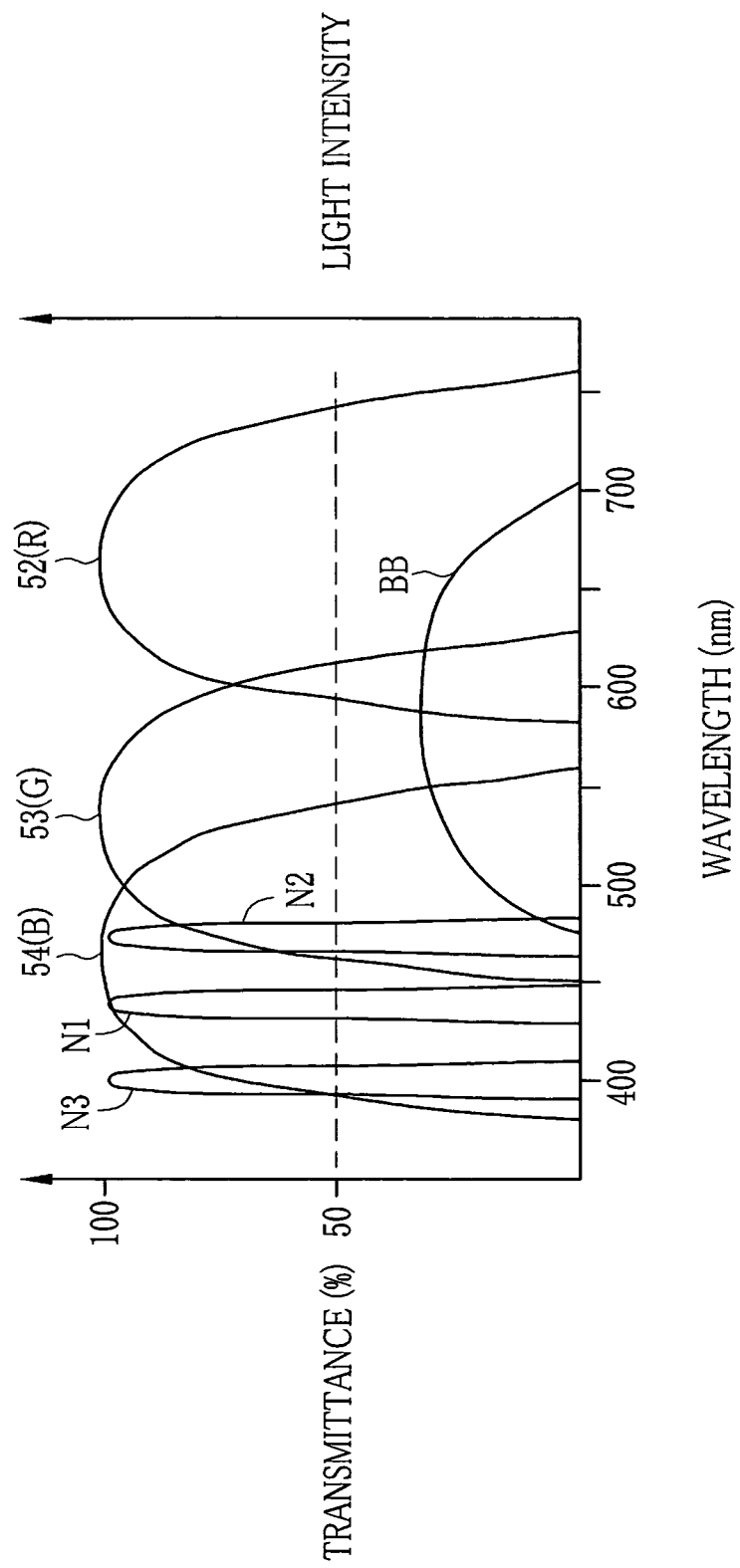
FIG. 3 is a graph showing spectral transmittance curves of color filters for red, green and blue.

The color filters for red (R), green (G) and blue (B) have spectral transmittances 52, 53 and 54, as shown in FIG. 3, respectively. Among the light entering the condenser lens 51, the broadband light BB has a wavelength of about 470 nm to 700 nm. Therefore, the RGB color filters respectively transmit such components of the broadband light BB that have wavelengths corresponding to their spectral transmittances 52, 53 and 54. Providing that image signal R designates an electric signal obtained through photo-electric conversion on the red pixels, image signal G designates an electric signal obtained through photo-electric conversion on the green pixels, and image signal B designates a signal obtained through photo-electric conversion on the blue pixels, a broadband image signal composed of the image signals RGB will be provided when the broadband light BB falls on the CCD 44.

On the other hand, among the light entering the condenser lens 51, the first narrowband ray N1 has a wavelength of 440±10 nm, so it can travel merely through the blue color filter. Accordingly, when the CCD 44 receives the first narrowband ray N1, the CCD 44 outputs a first narrowband image signal composed of a blue image signal. Since the second narrowband ray N2 has a wavelength of 470±10 nm, it can travel through the blue and green color filters. Accordingly, when the CCD 44 receives the second narrowband ray N2, the CCD 44 outputs a second narrowband image signal composed of blue and green image signals. Since the third narrowband ray N3 has a wavelength of 400±10 nm, it can travel through the blue color filter only. Accordingly, when the CCD 44 receives the third narrowband ray N3, the CCD 44 outputs a third narrowband image signal composed of a blue image signal.

The AFE 45 is constituted of a correlated double sampling circuit (CDS), an automatic gain control circuit (AGC), and an analog-to-digital converter (A/D), which are omitted from the drawings. The CDS processes the image signal from the CCD 44 through correlated double sampling, to eliminate noises that may be caused by the drive of the CCD 44. The AGC amplifies the image signal after the noise reduction through the CDS. The A/D converts the amplified image signal to a digital image signal of a predetermined bit number, and outputs the digital image signal to the processor 12.

The imaging controller 46 is connected to the controller 59 in the processor 12, to send a drive signal to the CCD 44 in response to a corresponding instruction from the controller 59. Based on the drive signal from the imaging controller 46, the CCD 44 outputs the image signal to the AFE 45 at a designated frame rate. In the first embodiment, when the system 10 is set at the ordinary lighting imaging mode, as shown in FIG. 4A, two operation steps are carried out during one frame capturing period: the broadband light BB being photo-electrically converted to electric charges and accumulated as the signal charges, and the accumulated signal charges being read as the broadband image signal. The system 10 repeats these operation steps so long as it is set at the ordinary lighting imaging mode.

On the other hand, when the system 10 is switched from the ordinary lighting imaging mode to the special lighting imaging mode, as shown in FIG. 4B, electric charges obtained through photo-electric conversion of the first narrowband ray N1 is accumulated as signal charges, and the accumulated signal charges is read as the first narrowband image signal in a first frame capturing period. After completing reading the first narrowband image signal, electric charges obtained through photo-electric conversion of the second narrowband ray N2 is accumulated as signal charges, and the accumulated signal charges is read as the second narrowband image signal in a second frame capturing period. After completing reading the second narrowband image signal, electric charges obtained through photo-electric conversion of the third narrowband ray N3 is accumulated as signal charges, and the accumulated signal charges is read as the third narrowband image signal in a third frame capturing period.

As shown in FIG. 2, the processor 12 includes a digital signal processor (DSP) 55, a frame memory 56, a blood vessel image producer 57, and a display control circuit 58, which are under the control of the controller 59. The DSP 55 processes the broadband image signal and the first to third narrowband image signals, as being output from the AFE 45 of the electronic endoscope, for color-separation, color-interpolation, white-balance adjustment, gamma correction and the like, to produce broadband image data and first to third narrowband image data. The frame memory 56 stores the broadband image data and the first to third narrowband image data as produced by the DSP 55. The broadband image data is color image data including data of the captured three-color images RGB.

The blood vessel image producer 57 includes a luminance ratio calculator 60, a correlation memory 61, a vessel depth and oxygen saturation calculator 62, a vessel depth image producer 63 and an oxygen saturation image producer 64. The luminance ratio calculator 60 identifies such an image area that contains blood vessels, hereinafter called the vascular area, on the basis of the first to third narrowband image data stored in the frame memory 56. The luminance ratio calculator 60 calculates a first luminance ratio S1/S3 between the first and third narrowband images with respect to individual pixels in the vascular area, wherein S1 represents the luminance of one pixel of the first narrowband image, whereas S3 represents the luminance of a corresponding pixel of the third narrowband image, the corresponding pixel representing the same location of the subject as the one pixel of the first narrowband image. The luminance ratio calculator 60 also calculates a second luminance ratio S2/S3 between the second and third narrowband images, wherein S2 represents the luminance of a corresponding pixel of the second narrowband image, which represents the same location of the subject as the corresponding pixels of the first and third narrowband images. Note that the method of identifying the vascular area may for example be a method of identifying the vascular area on the basis of differences in luminance between blood vessels and other body portions.

Figure 5:
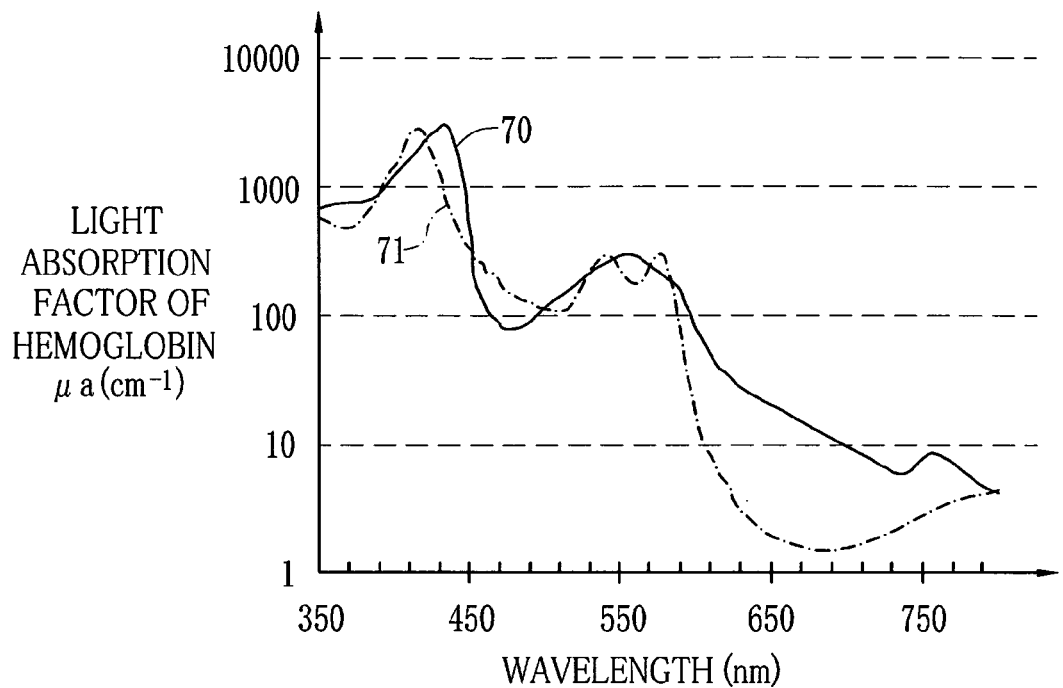
FIG. 5 is a graph showing light absorption coefficients of hemoglobin.

The correlation memory 61 memorizes correlation between the first and second luminance ratios S1/S3 and S2/S3 and the oxygen saturation and the blood vessel depth. The correlation may be acquired from analyses of an enormous amount of the first to third narrowband image data obtained and accumulated through diagnoses and the like, on the basis of light absorption coefficient of hemoglobin contained in the blood vessels. As shown in FIG. 5, hemoglobin in the blood vessels has such light absorption characteristics that the light absorption coefficient μa varies depending on the wavelength of the illumination light. The light absorption coefficient μa indicates the degree of light absorbance of hemoglobin, i.e. the magnitude of light absorption in hemoglobin. The light absorption coefficient is a coefficient used in a formula expressing the attenuation of light projected onto hemoglobin: Ioexp(−μa×x), wherein Io stands for the intensity of light projected from a light source toward a subject tissue, and x (cm) stands for the depth to a blood vessel in the subject tissue.

Since reduced hemoglobin, which is not combined with oxygen, has a different light absorption characteristic curve 70 from a light absorption characteristic curve 71 of oxygenated hemoglobin that is combined with oxygen, the light absorbance of the reduced hemoglobin differs from that of the oxygenated hemoglobin, except at isosbestic points (intersections between the curves 70 and 71), at which reduced hemoglobin and oxygenated hemoglobin have the same degree of light absorbance (the same light absorption coefficient μa). Because of the difference in light absorbance between reduced hemoglobin and oxygenated hemoglobin, the luminance of an identical blood vessel will vary depending upon the percentage of oxygenated hemoglobin in that vessel, even while the vessel is illuminated with light of constant intensity and wavelength. In addition, the light absorption coefficient μa and hence the luminance will change with the wavelength of the illumination light, even if the light intensity is unchanged.

In view of the above light absorption characteristics of hemoglobin, as shown in FIG. 5, the light absorbance of blood vessels will vary depending on the oxygen saturation, especially at wavelengths of 445 nm and 473 nm. Since the ray of longer wavelength can reach the deeper inside the tissues, the first to third narrowband rays N1 to N3 preferably include at least a narrowband ray of a wavelength range having a center wavelength of not more than 450 nm, in order to cover the wide depth range in acquiring information about blood vessel depth. In the first embodiment, the first and the third narrowband rays N1 and N3 satisfy this condition. Even where the oxygen saturation is the same, if the wavelength of the illumination light is different, the light absorption coefficient will change, and hence the reaching depth of the illumination light into the mucous membrane will change. Accordingly, the correlation between the luminance ratio and the blood vessel depth may be determined by making use of the property of light that the depth of reach will vary depending on the wavelength.

Figure 6:
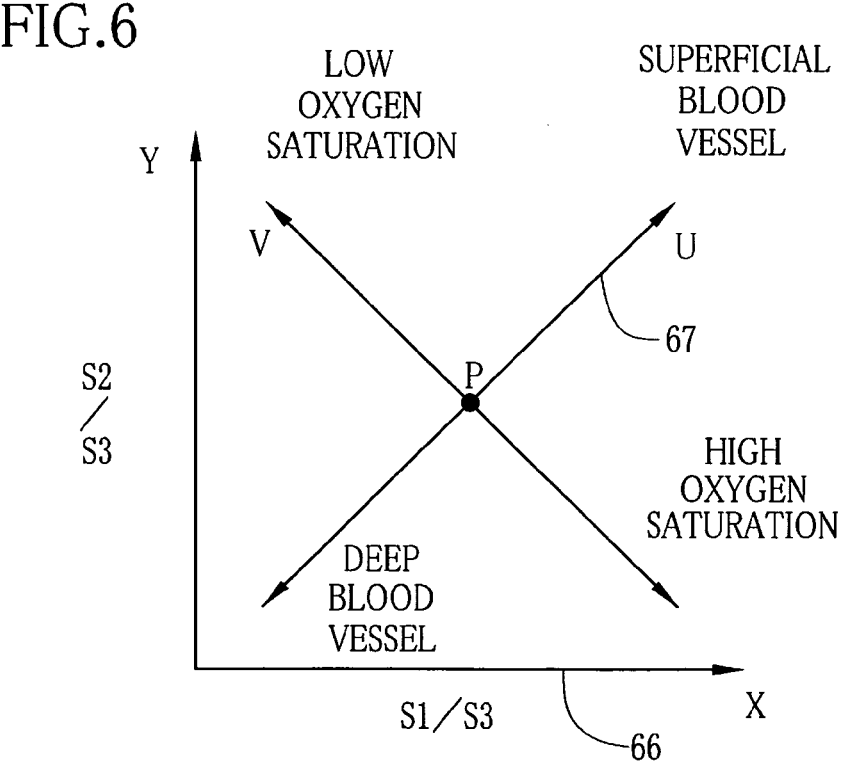
FIG. 6 is a graph showing correlation between luminance ratios S1/S3 and S2/S3, and blood vessel depth and oxygen saturation.

The correlation memory 61 memorizes the correlation as shown in FIG. 6, wherein coordinates of a luminance coordinate system 66 that represents the first and second luminance ratios S1/S3 and S2/S3 are correlated with coordinates of another luminance coordinate system 67 that represents the oxygen saturation and the blood vessel depth. The luminance coordinate system 66 is an X-Y coordinate system, wherein X axis represents the first luminance ratio S1/S3 and Y axis represents the second luminance ratio S2/S3. The luminance coordinate system 67 is a U-V coordinate system provided on the luminance coordinate system 66, wherein U axis represents the blood vessel depth, and V axis represents the oxygen saturation. The U axis has a positive inclination because the blood vessel depth has a positive correlation to the luminance coordinate system 66. Concerning the U axis, upper-right direction indicates decreasing blood vessel depth, and lower-left direction indicates increasing blood vessel depth. On the other hand, the V axis has a negative inclination because the oxygen saturation has a negative correlation to the luminance coordinate system 66. Concerning the V axis, upper-left direction indicates descending oxygen saturation, and lower-right direction indicates ascending oxygen saturation. It is to be noted that the information on the blood vessel depth may be numerical values that increase with the blood vessel depth. Also the information on the oxygen saturation may be numerical values in the same way as the information on the blood vessel depth.

In the luminance coordinate system 67, the U axis and the V axis orthogonally intersect at a point P. This is because oxygenated hemoglobin has a reversed magnitude relation between the light absorbance to the first narrowband ray N1 and the light absorbance to the second narrowband ray N2 from that of reduced hemoglobin. Specifically, as shown in FIG. 5, to the first narrowband ray N1 having the wavelength of 440±10 nm, the light absorption coefficient of reduced hemoglobin 70 is higher than the light absorption coefficient of oxygenated hemoglobin 71, of which the oxygen saturation is higher than the oxygen saturation of reduced hemoglobin. On the contrary, to the second narrowband ray N2 having the wavelength of 470±10 nm, the light absorption coefficient of oxygenated hemoglobin 71 is higher than the light absorption coefficient of reduced hemoglobin 70. That is, the order in magnitude of the light absorption coefficient to the first narrowband ray N1 and the light absorption coefficient to the second narrowband ray N2 is reversed between the reduced hemoglobin 70 and the oxygenated hemoglobin 71. It is to be noted that the U axis and V axis would not be orthogonal if the first to third narrowband rays N1 to N3 were set in such wavelength ranges, to which the magnitude relation between the light absorption coefficient of oxygenated hemoglobin 71 and the light absorption coefficient of reduced hemoglobin 70 is unchanged. Meanwhile, to the third narrowband ray N3 having the wavelength of 400±10 nm, the light absorption coefficient of oxygenated hemoglobin is approximately equal to that of reduced hemoglobin.

On the basis of the correlation stored in the correlation memory 61, the vessel depth and oxygen saturation calculator 62 determines the oxygen saturation and the blood vessel depth corresponding to the first and second luminance ratios S1/S3 and S2/S3 that are calculated by the luminance ratio calculator 60. Hereinafter, among the first and second luminance ratios S1/S3 and S2/S3 calculated by the luminance ratio calculator 60, the first luminance ratio at a particular pixel in the vascular area will be expressed as S1*/S3*, and the second luminance ratio on the particular pixel will be expressed by S2*/S3*.

Figure 7A:
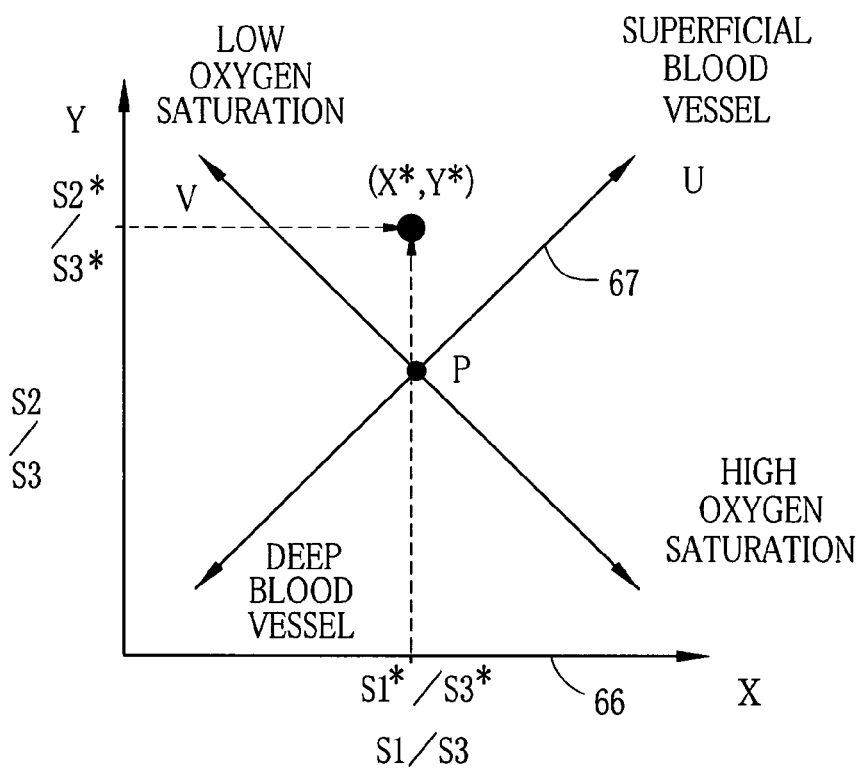
FIG. 7A is an explanatory diagram illustrating a method of deriving coordinates $(X^*, Y^*)$ of a luminance coordinate system from the first and second luminance ratios $S1^*/S3^*$ and $S2^*/S3^*$.
Figure 7B:
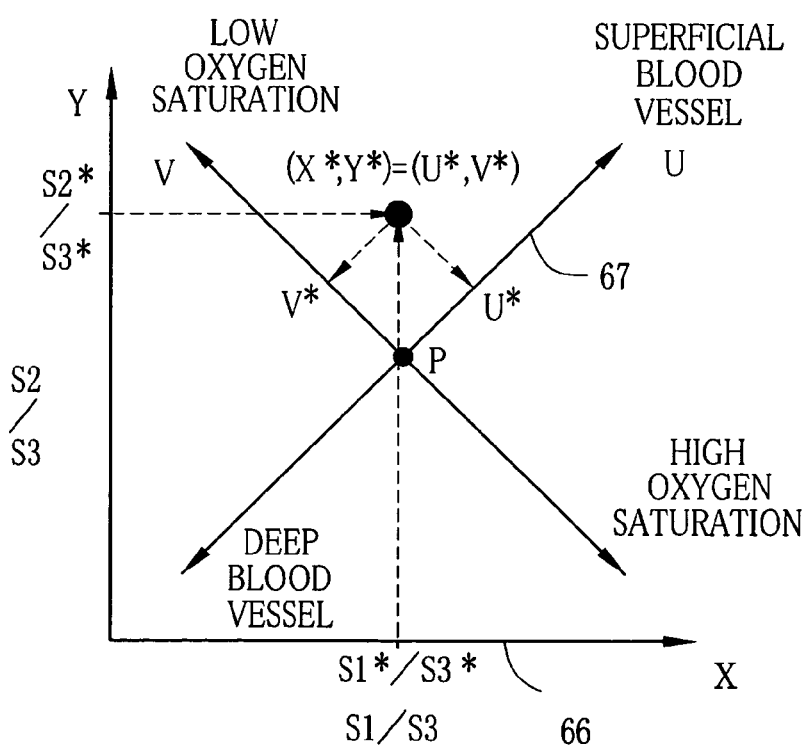
FIG. 7B is an explanatory diagram illustrating a method of deriving coordinates $(U^*, V^*)$ of a vascular information coordinate system, which correspond to the coordinates $(X^*, Y^*)$ of the luminance coordinate system.

The vessel depth and oxygen saturation calculator 62 determines coordinates (X*, Y*) in the luminance coordinate system 66, which correspond to the first and second luminance ratios S1*/S3* and S2*/S3*, as shown in FIG. 7A. After determining the coordinates (X*, Y*), the calculator 62 determines coordinates (U*, V*) in the luminance coordinate system 67, which correspond to the coordinates (X*, Y*) as shown in FIG. 7B. Thus, the blood vessel depth U* and the oxygen saturation V* are determined with respect to the particular pixel in the vascular area.

The vessel depth image producer 63 includes a color table 63a that assigns color information of different colors to different ranges of the blood vessel depth. For example, the color table 63a assigns blue to blood vessels in a superficial range, green to blood vessels in a middle range, and red to blood vessels in a deep range. Thus, blood vessels of different depth ranges are displayed in different colors within the image, to be clearly distinguishable from one another. With reference to the color table 63a, the vessel depth image producer 63 decides the color information to each pixel in the vascular area according to the blood vessel depth U* that is calculated for each pixel by the vessel depth and oxygen saturation calculator 62.

After deciding the color information to every pixel inside the vascular area, the vessel depth image producer 63 reads out the broadband image data from the frame memory 56, to reflect the color information on the broadband light image data. Thus, data of a vessel depth image is produced, which informs of the depth levels of the contained blood vessels. The vessel depth image data is stored again in the frame memory 56. Alternatively, the color information may be reflected on either of the first to third narrowband image data or a composite image composed of the first to third narrowband image data, not on the broadband light image data.

The oxygen saturation image producer 64 includes a color table 64a that assigns color information of different colors to different levels of the oxygen saturation. For example, the color table 63a assigns cyan to blood vessels of a low oxygen saturation level, magenta to blood vessels of a middle oxygen saturation level, and yellow to blood vessels of a high oxygen saturation level. Thus, blood vessels of different oxygen saturation levels are displayed in different colors within the image, to be clearly distinguishable from one another. Like the vessel depth image producer 63, the oxygen saturation image producer 64 refers to the color table 64a to decide the color information to each pixel in the vascular area according to the oxygen saturation V* that is calculated for each pixel by the vessel depth and oxygen saturation calculator 62. By reflecting the color information on the broadband image data, the oxygen saturation image producer 64 produces data of an oxygen saturation image. The oxygen saturation image data is stored in the frame memory 56, like the vessel depth image data.

Figure 8:
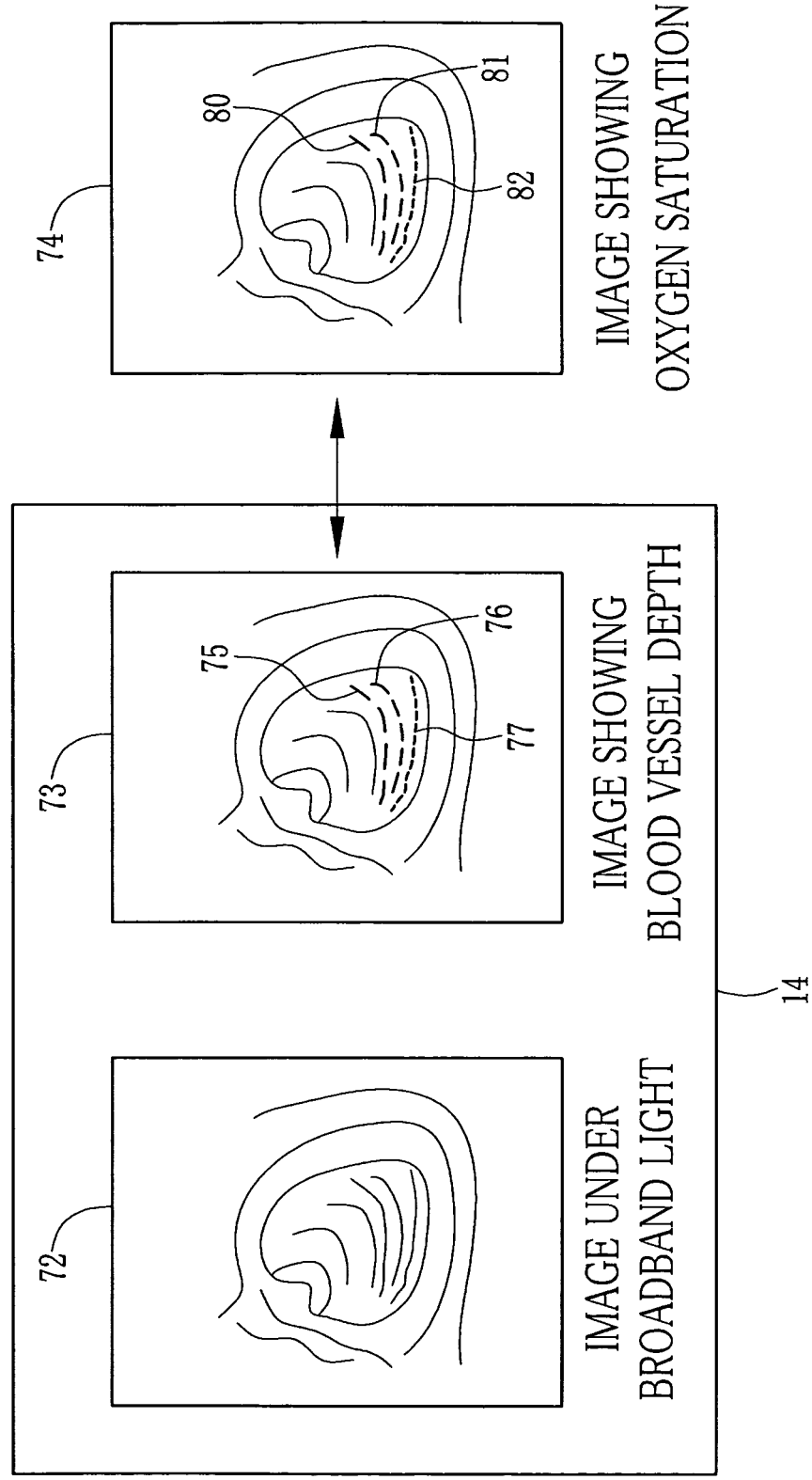
FIG. 8 is a diagram illustrating a monitor screen which alternately displays an image showing information on the vessel depth or an image showing information on the oxygen saturation.
Figure 9:
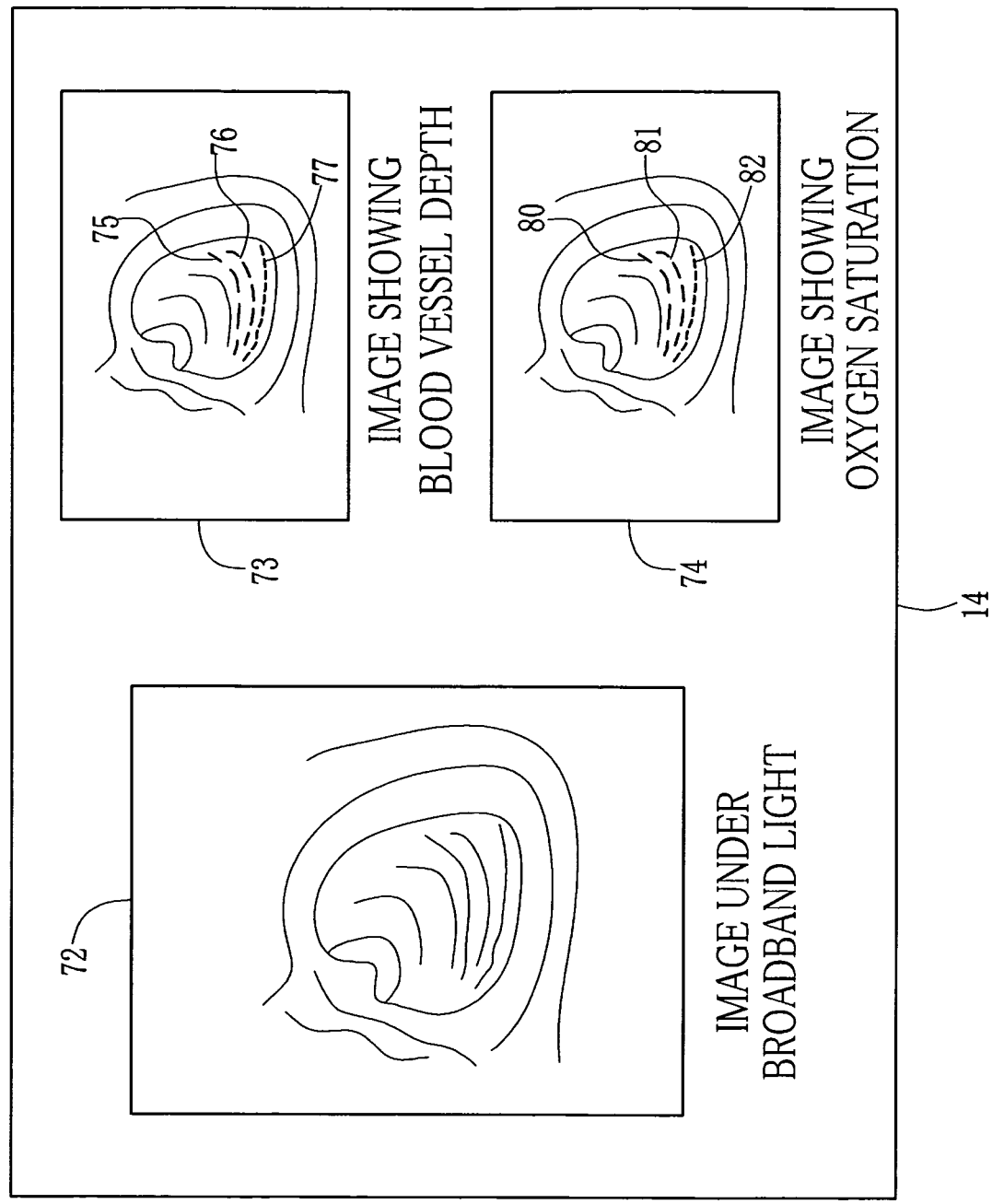
FIG. 9 is a diagram illustrating a monitor screen displaying both an image showing information on the vessel depth and an image showing information on the oxygen saturation at once.

The display control circuit 58 reads out one or more images from the frame memory 56, to be displayed on the monitor 14. There may be a variety of patterns available for displaying the images. For example, as shown in FIG. 8, the monitor 14 displays an image 72 taken under the broadband light on one side of a screen, and an image 73 showing vessel depth or an image 74 showing oxygen saturation level on the other side of the screen, wherein the images 73 and 74 are interchangeable in response to an image changing switch 68 (see FIG. 2). Alternatively, the vessel depth image 73 and the oxygen saturation image 74 may be displayed at once on the same screen, as shown in FIG. 9.

The vessel depth image 73 may contain an image 75 of superficial blood vessels, an image 76 of middle-layer vessels, and an image 77 of deep blood vessels. According to the present embodiment, the image 75 is displayed in blue, the image 76 is displayed in green, and the image 77 is displayed in red. On the other hand, in the oxygen saturation image 74, an image 80 of those blood vessels which are at the low oxygen saturation level is displayed in cyan, and an image 81 of blood vessels at the middle oxygen saturation level is displayed in magenta, whereas an image 82 of blood vessels at the high oxygen saturation level is displayed in yellow.

Figure 10:
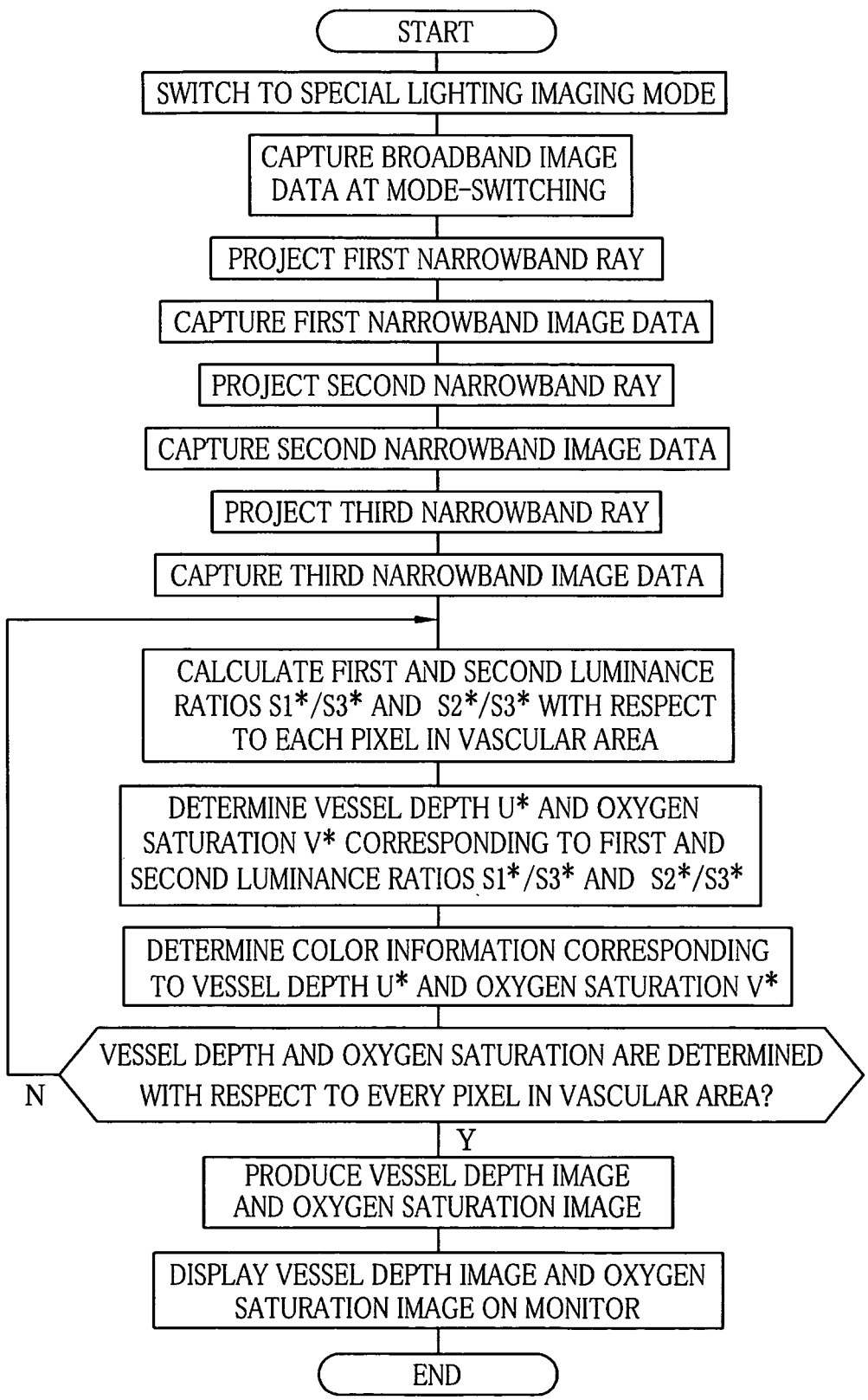
FIG. 10 is a flowchart illustrating the procedure of calculating information on blood vessel depth and oxygen saturation, and producing an image showing information on the vessel depth and an image showing information on the oxygen saturation, these images reflecting the information.

Now the sequence of acquiring information on the depth and oxygen saturation level of blood vessels and producing an image showing information on the vessel depth and an image showing information on the oxygen saturation level will be described with reference to the flowchart shown in FIG. 10. First, the console 23 is operated to switch the system 10 from the ordinary lighting imaging mode to the special lighting imaging mode. When the system 10 is switched to the special lighting imaging mode, broadband image data obtained at this moment is stored in the frame memory 56, for use in producing the vessel depth image or the oxygen saturation image. Note that broadband image data obtained before the system 10 is switched to the special lighting imaging mode may be used for producing the vessel depth image or the oxygen saturation image.

When the controller 59 sends an illumination stop command to the shutter driver 32, the shutter driver 32 drives the shutter 31 to move into the optical path of the broadband light BB to interrupt the broadband light BB from the body cavity. When the broadband light BB is interrupted, the controller 59 sends an illumination start command to the light source switching section 37. Then the light source switching section 37 turns the first narrowband light source 33 ON, to project the first narrowband ray N1 into the body cavity. While the first narrowband ray N1 is being projected into the body cavity, the controller 59 sends an imaging start command to the imaging controller 46. Thereby, a first narrowband image signal is obtained under the first narrowband ray N1, and is sent through the AFE 45 to the DSP 55. The DSP 55 produces the first narrowband image data from the first narrowband image signal, and the first narrowband image data is stored in the frame memory 56.

When the first narrowband image data has been stored in the frame memory 56, the controller 59 outputs a light source switching command to the light source switching section 37, to switch the body cavity illumination light from the first narrowband ray N1 to the second narrowband ray N2. Then the second narrowband image signal is captured under the second narrowband ray N2 in the same way as for the first narrowband ray N1, and the second narrowband image data is produced from the second narrowband image signal. The second narrowband image data is stored in the frame memory 56.

When the second narrowband image data is stored in the frame memory 56, the controller 59 outputs a light source switching command to the light source switching section 37, to switch the illumination light from the second narrowband ray N2 to the third narrowband ray N3. Then the third narrowband image signal is captured under the third narrowband ray N3 in the same way as for the second narrowband ray N2, and the third narrowband image data is produced from the third narrowband image signal. The third narrowband image data is stored in the frame memory 56.

When the broadband image data and the first to third narrowband image data have been stored in the frame memory 56, the luminance ratio calculator 60 extracts a vascular area containing blood vessels from the first narrowband image data, the second narrowband image data, the third narrowband image data. Thereafter, the luminance ratio calculator 60 calculates the first luminance ratio S1*/S3* between the first and the third narrowband image data, and the second luminance ratio S2*/S3* between the second and the third narrowband image data, with respect to a particular pixel in the vascular area.

Next, the vessel depth and oxygen saturation calculator 62 determines the coordinates (X*, Y*) in the luminance coordinate system, which correspond to the first and second luminance ratios S1*/S3* and S2*/S3*, with reference to the correlation data stored in the correlation memory 61. The vessel depth and oxygen saturation calculator 62 also determines the coordinates (U*, V*) in the luminance coordinate system, which correspond to the coordinates (X*, Y*). Thus, the vessel depth and oxygen saturation calculator 62 acquires information on the blood vessel depth U* and the oxygen saturation V* with respect to the particular pixel in the vascular area.

After the blood vessel depth U* and the oxygen saturation V* are detected with respect to the particular pixel, the vessel depth image producer 63 determines the color information corresponding to the blood vessel depth U* with reference to the color table 63a, and also determines the color information corresponding to the oxygen saturation V* with reference to the color table 64a. The determined color information is stored in a RAM that is not shown but provided in the processor 12.

After storing the color information in the RAM, the vessel depth and oxygen saturation calculator 62 determines the blood vessel depth U* and the oxygen saturation V* with respect to every pixel in the vascular area in the same way as described above, and also determines the color information corresponding to the blood vessel depth U* and the color information corresponding to the oxygen saturation V*.

When the information on the blood vessel depth and the oxygen saturation and the color information corresponding to these values are acquired with respect to every pixel in the vascular area, the vessel depth image producer 63 reads out the broadband image data from the frame memory 56, and reflects the color information corresponding to the blood vessel depths of the respective pixels on the read broadband image data, to produce the vessel depth image data. Like the vessel depth image producer 63, the oxygen saturation image producer 64 produces the oxygen saturation image data. The vessel depth image data and the oxygen saturation image data are stored in the frame memory 56.

Then, the display control circuit 58 reads out the broadband image data, the vessel depth image data, and the oxygen saturation image data from the frame memory 56, to display based on these data, the broadband light image 72, the vessel depth image 73, and the oxygen saturation image 74 on the monitor 14, as shown in FIG. 8 or 9. In FIG. 8, the monitor 14 displays the broadband light image 72, which is taken in the ordinary lighting mode, and the vessel depth image 73 or the oxygen saturation image side by side on the same screen. In FIG. 9, the monitor 14 displays the broadband light image 72, the vessel depth image 73, and the oxygen saturation image 74 simultaneously.

The endoscope system 10 of the first embodiment projects the first to third narrowband rays N1 to N3 one after another to capture one frame for one narrowband. Thus, totally three image frames of the same subject are successively captured in one imaging cycle of the special lighting imaging mode. Alternatively, in the second embodiment of the present invention, as shown in FIG. 11, the third narrowband ray N3 is first projected into the body cavity to capture an image frame, and then a composite narrowband ray composed of the first and second narrowband rays N1 and N2 is projected to capture a second image frame. From these two image frames, the first to third narrowband image data is produced. That is, the number of image frames necessary for producing the first to third narrowband image data is reduced from three to two as compared to the first embodiment. The reduced number of image frames is preferable, because pixel deviations between the frames, which may be caused by the movement of the subject body under inspection or the movement of the probing portion of the endoscope, tend to be suppressed. Since the blood vessel depth and the oxygen saturation are determined based on the luminance ratios between the corresponding pixels that represent the same location of the subject in the first to third narrowband image data, the less pixel deviation will lead to the higher accuracy.

Because the electronic endoscope system of the second embodiment may have the same structure as the electronic endoscope system 10 of the first embodiment, except the sequence of switching between the first to third narrowband light sources 33 to 35, and the image signals from the CCD 44, the structure of the second embodiment is not illustrated in the drawings, and only the essential feature of the second embodiment will be explained below.

In the second embodiment, the first to third narrowband light sources 33 to 35 are turned OFF in the ordinary lighting imaging mode. When the system is switched from the ordinary lighting imaging mode to the special lighting imaging mode, the third narrowband light source 35 is turned ON by the light source switching section 37. Thus, an image frame is captured from the subject tissue while the third narrowband ray N3 is being projected into the body cavity. When the imaging under the third narrowband ray N3 is complete, the controller 59 gives an instruction to switch the light source, upon which the third narrowband light source 35 is turned OFF, and the first and second narrowband light sources 33 and 34 are turned ON. Then, a second image frame is captured while a composite ray composed of the first and second narrowband rays N1 and N2 is being projected into the body cavity. When the second image frame has been captured, the first and second narrowband light sources 33 and 34 are turned OFF.

In the second embodiment, image signals output from the CCD 44 are as follows: Since the third narrowband ray N3, which is projected first into the body cavity, can travel only through the blue filter, an image signal B1 is obtained through the blue pixels, having luminance L3 based on the third narrowband ray N3. As for the composite narrowband ray projected after the third narrowband ray N3, the first narrowband ray N1 travels through the blue filter, and the second narrowband ray N2 travels through the blue and green filters. Therefore, an image signal B2 including luminance L1 based on the first narrowband ray N1 and luminance L2 based on the second narrowband ray N2 is obtained through the blue pixels, and an image signal G2 having luminance L2 based on the second narrowband ray N2 is obtained through the green pixels. Consequently, the CCD 44 outputs the following image signals to the DSP 55 of the processor 12:

Image signal $B1$=luminance $L3$

Image signal $B2$=luminance $L1$+luminance $L2$

Image signal $G2$=luminance $L2$

The DSP 55 produces the first to third narrowband image data from the image signals B1, B2 and G2. Since the image signal B1 merely represents the luminance L3 that is based on the third narrowband ray N3, the third narrowband image data may be obtained from the image signal B1. Likewise, since the image signal G2 merely represents the luminance L2 that is based on the second narrowband ray N2, the second narrowband image data may be obtained from the image signal G2. The first narrowband image data, on the other hand, may be obtained by separating the luminance L2 from the image signal B2 using a calculation: B2−(constant)×G2, wherein the constant is determined by the ratio of intensity between the first narrowband ray N1 and the second narrowband ray N2. The obtained first to third narrowband image data are stored in the frame memory 56.

As a variation of the second embodiment, it is possible to project the first narrowband ray N1 first, and then a composite narrowband ray composed of the second and third narrowband rays N2 and N3, as shown in FIG. 12. In that case, the following image signals may be obtained:

Image signal $B1$=luminance $L1$ based on the first narrowband ray N1

Image signal $B2$=luminance $L2$ based on the second narrowband ray $N2$+luminance $L3$ based on the third narrowband ray $N3$ Image signal $G2$=luminance $L2$ based on the second narrowband ray $N2$ In the case of FIG. 12, the DSP 55 produces the first narrowband image data from the image signal B1, the second narrowband image data from the image signal G2. On the other hand, the third narrowband image data may be obtained by separating the luminance L2 from the image signal B2 using a calculation: B2−(constant)×G2, wherein the constant is determined by the ratio of intensity between the second narrowband ray N2 and the third narrowband ray N3.

Figure 13:
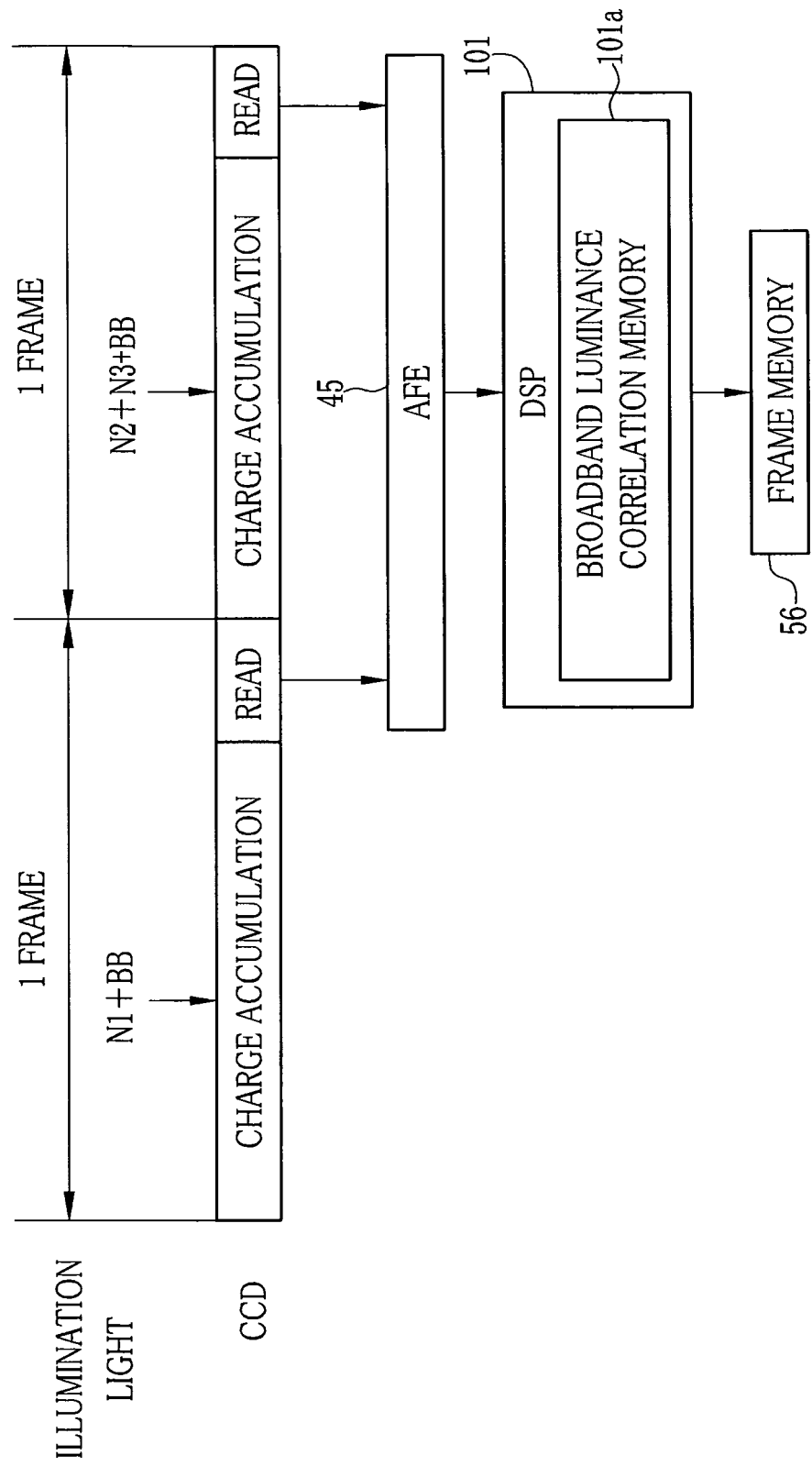
FIG. 13 is an explanatory diagram illustrating an imaging operation in a third embodiment of the present invention.

Unlike the first and second embodiments, wherein the broadband light BB is not projected together with the first to third narrowband rays N1 to N3, the third embodiment of the present invention, as shown in FIG. 13, first projects the first narrowband ray N1 and the broadband light BB at the same time to capture a first image frame, and then projects the second narrowband ray N2, the third narrowband ray N3 and the broadband light BB all at once to capture a second image frame. From these two frames of image signal, the first to third narrowband image data are produced. Moreover, in the third embodiment, the broadband image data may be produced simultaneously with the first to third narrowband image data. Therefore, when the broadband image is displayed together with the information about the blood vessel depth and/or the oxygen saturation on the monitor 14, as shown in FIGS. 8 and 9, there is no time lag between the broadband image and the information. This feature of the third embodiment is superior to the first and the second embodiments.

The electronic endoscope system of the third embodiment may have the same structure as the electronic endoscope system 10 of the first embodiment, except that the DSP 55 of the first embodiment is replaced with a DSP 101 as shown in FIG. 13, and that the driving operation of the shutter 31, the switching sequence between the first to third narrowband light sources 33 to 35 and image signals output from the CCD 44 are different from those in the above embodiments. Therefore, the structure of the electronic endoscope system of the third embodiment is omitted from the drawings, and the following description will relate merely to essential features of the third embodiment.

In the third embodiment, the shutter 31 is always kept away from the optical path of the broadband light source 30, and the broadband light source 30 is kept ON during the operation of the electronic endoscope 11. Therefore, the broadband light BB continues being projected into the body cavity. On the other hand, the first to third narrowband light sources 33 to 35 are turned OFF in the ordinary lighting imaging mode. When the system is switched from the ordinary lighting imaging mode to the special lighting imaging mode, the first narrowband light source 33 is first turned ON by the light source switching section 37. While the first narrowband ray N1 and the broadband light BB are being projected into the body cavity, a first image frame is captured from the subject tissues. After the first image frame is captured, the controller 59 outputs a switching command, upon which the first narrowband light source 33 is turned OFF, and the second and third narrowband light sources 34 and 35 are turned ON. Then, a second image frame is captured while the second narrowband ray N2, the third narrowband ray N3 and the broadband light BB are being projected into the body cavity. Thereafter, the second and the third narrowband light sources 34 and 35 are turned OFF.

In the third embodiment, the CCD 44 outputs the image signals in the following manner. Of the light components that fall on the photo sensing surface 44a of the CCD 44 while the first narrowband ray N1 and the broadband light BB are being projected, the first narrowband ray N1 travels through the blue filter, whereas the broadband light BB travels through both the blue and green filters. As a result, an image signal B1 representing luminance L1 based on the first narrowband ray N1 and luminance Broad_B1 based on the broadband light BB is obtained through the blue pixels of the CCD 44, and an image signal G1 having luminance Broad_G1 based on the broadband light BB is obtained through the green pixels of the CCD 44.

On the other hand, while the second and third narrowband rays N2 and N3 and the broadband light BB are being projected, the second narrowband ray N2 and the broadband light BB travel through both the blue and green filters, whereas the third narrowband ray N3 travels merely through the blue filter. As a result, an image signal B2, which consists of luminance L2 based on the second narrowband ray N2, luminance L3 based on the third narrowband ray N3, and luminance Broad_B2 based on the broadband light BB, is obtained through the blue pixels of the CCD 44. Also an image signal G2, which consists of the luminance L2 and luminance Broad_G2 based on the broadband light BB, is obtained through the green pixels of the CCD 44. Consequently, the CCD 44 outputs the following image signals to the DSP 101:

Image signal $B1$=luminance $L1$+luminance Broad $B1$

Image signal $G1$=luminance Broad $G1$

Image signal $B2$=luminance $L2$+luminance $L3$+luminance Broad_$B2$

Image signal $G2$=luminance $L2$+luminance Broad $G2$

The DSP 101 of the third embodiment includes a broadband luminance correlation memory 101a that memorizes correlation between the luminance Broad_B1, the luminance Broad_G1, the luminance Broad_B2, and the luminance Broad_G2. The correlation may be acquired through an analysis of an enormous volume of image data obtained from diagnoses, inspections and the like. With reference to the broadband luminance correlation memory 101a, the DSP 101 determines those luminance values Broad_B1, Broad_B2 and Broad_G2 which have correlation to the luminance value Broad_G1. Then, the DSP 101 separates the determined luminance values Broad_B1, Broad_B2 and Broad_G2 from the image signals B1, B2 and G2 respectively, to obtain the following image signals:

Image signal $B1^*$=luminance $L1$

Image signal $B2^*$=luminance $L2$+luminance $L3$

Image signal $G2^*$=luminance $L2$

The DSP 101 derives the first narrowband image data from the image signal B1*, and the second narrowband image data from image signal G2*. On the other hand, the third narrowband image data is obtained by separating the luminance value L2 from image signal B2* using a calculation: B2*−(constant)×G2*, wherein the constant is determined by the ratio of intensity between the second and third narrowband rays. The first to third narrowband image data are stored in the frame memory 56.

In the third embodiment, luminance values Broad_B1, Broad_G1, Broad_B2 and Broad_G2 may be obtained based on the broadband light BB in the special lighting imaging mode. Therefore, not only the narrowband image data (data of special images taken under the special lighting) but also the broadband image data (data of a full-color image taken under the ordinary lighting) may be obtained at once. Also in the third embodiment, the first narrowband ray N1 and the third narrowband ray N3 are interchangeable, like the variation from FIG. 11 to FIG. 12 in the second embodiment.

Figure 14:
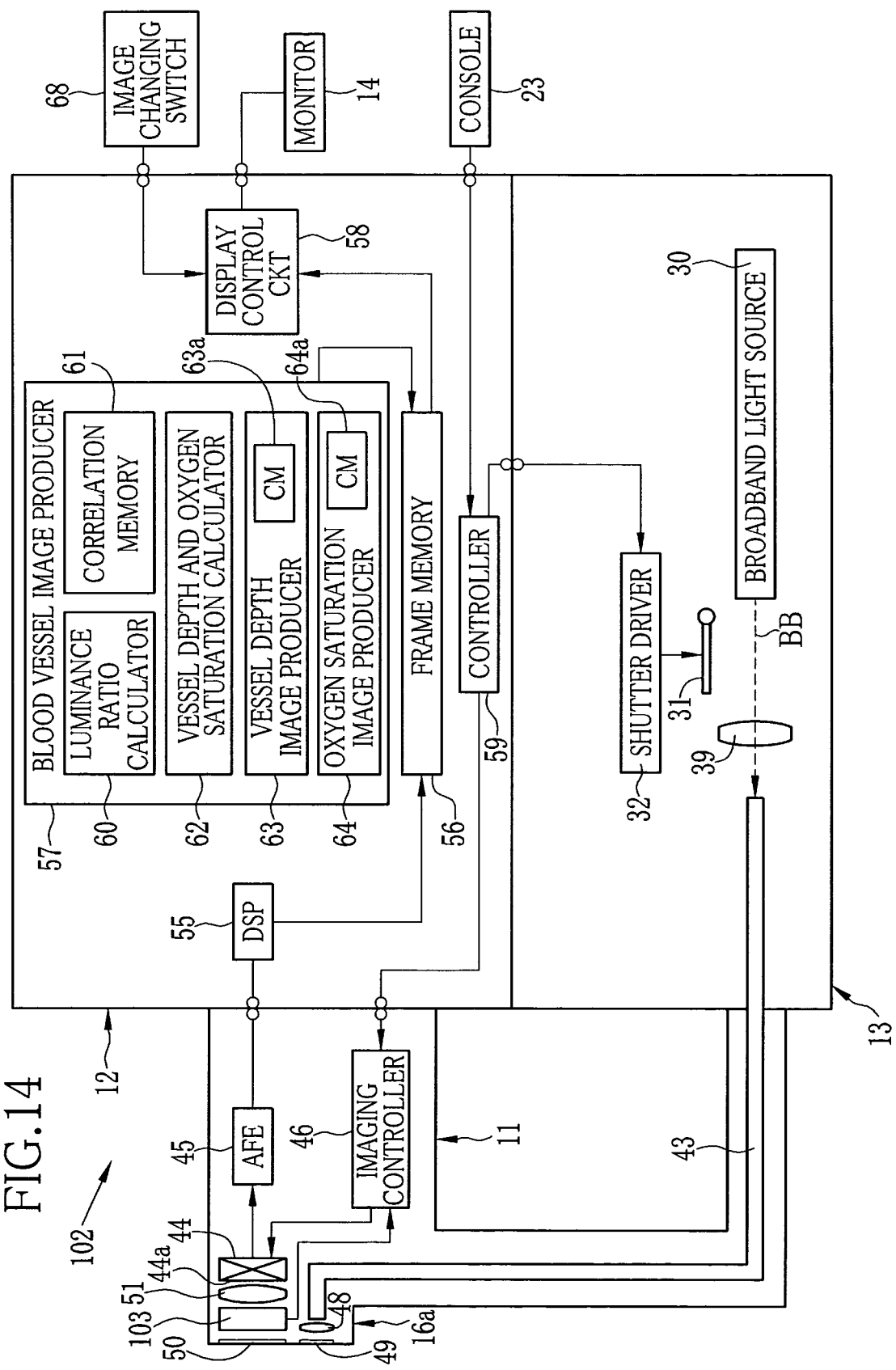
FIG. 14 is a block diagram illustrating the circuitry of an electronic endoscope system according to a fourth embodiment of the present invention.

In the fourth embodiment of the present invention, as shown in FIG. 14, the first to third narrowband light sources 33 to 35 are not installed, but an acousto-optical tunable filter 103 is provided in an electronic endoscope 11, so that the broadband light BB as projected from the endoscope 11 and reflected from the subject tissues is sequentially separated into the first to third narrowband rays N1 to N3 through the acousto-optical tunable filter 103. As a result, a CCD 44 sequentially captures images based on the spectrally-filtered rays. Otherwise, an electronic endoscope system 102 of the fourth embodiment may have the same configuration as the electronic endoscope system 10 of the first embodiment. Therefore, merely essential features of the fourth embodiment will be described.

In the electronic endoscope system 102 of the fourth embodiment, the acousto-optical tunable filter 103 is disposed between an observation window 50 and a condenser lens 51. The acousto-optical tunable filter 103 separates the broadband light BB, as being reflected from the body cavity, sequentially into the first to third narrowband rays N1 to N3. For example, the acousto-optical tunable filter 103 first separates the first narrowband ray N1 from the reflected broadband light BB, and then separate the second narrowband ray N2, and thereafter the third narrowband ray N3 from the reflected broadband light BB. However, the sequence of spectral separation is not limited to this order. The acousto-optical tunable filter 103 is connected to the imaging controller 46, to send a spectral switching signal to the imaging controller 46 each time the acousto-optical tunable filter 103 switches the turn of spectral separation among the three narrowband rays. In response to the spectral switching signal, the imaging controller 46 outputs an imaging signal to the CCD 44. Thus, the CCD 44 captures an image signal while it receives one of the three narrowband rays from the acousto-optical tunable filter 103. Consequently, the CCD 44 outputs the first to third narrowband image signals, like the first embodiment.

It is also possible to provide spectral filters on a CCD in place of the color filters on the CCD 44, in order to obtain the narrowband rays N1 to N3 from the broadband light BB as it enters through the tip portion of the electronic endoscope 11. Concretely, a first kind of filters allowing only the first narrowband ray N1 to pass therethrough, a second kind of filters allowing only the second narrowband ray N2 to pass therethrough, and a third kind of filters allowing only the third narrowband ray N3 to pass therethrough may be arranged in front of pixels of the CCD. The CCD with the spectral filters makes it possible to separate the broadband light BB into the narrowband rays, without the need for the acousto-optical tunable filter 103.

Figure 15:
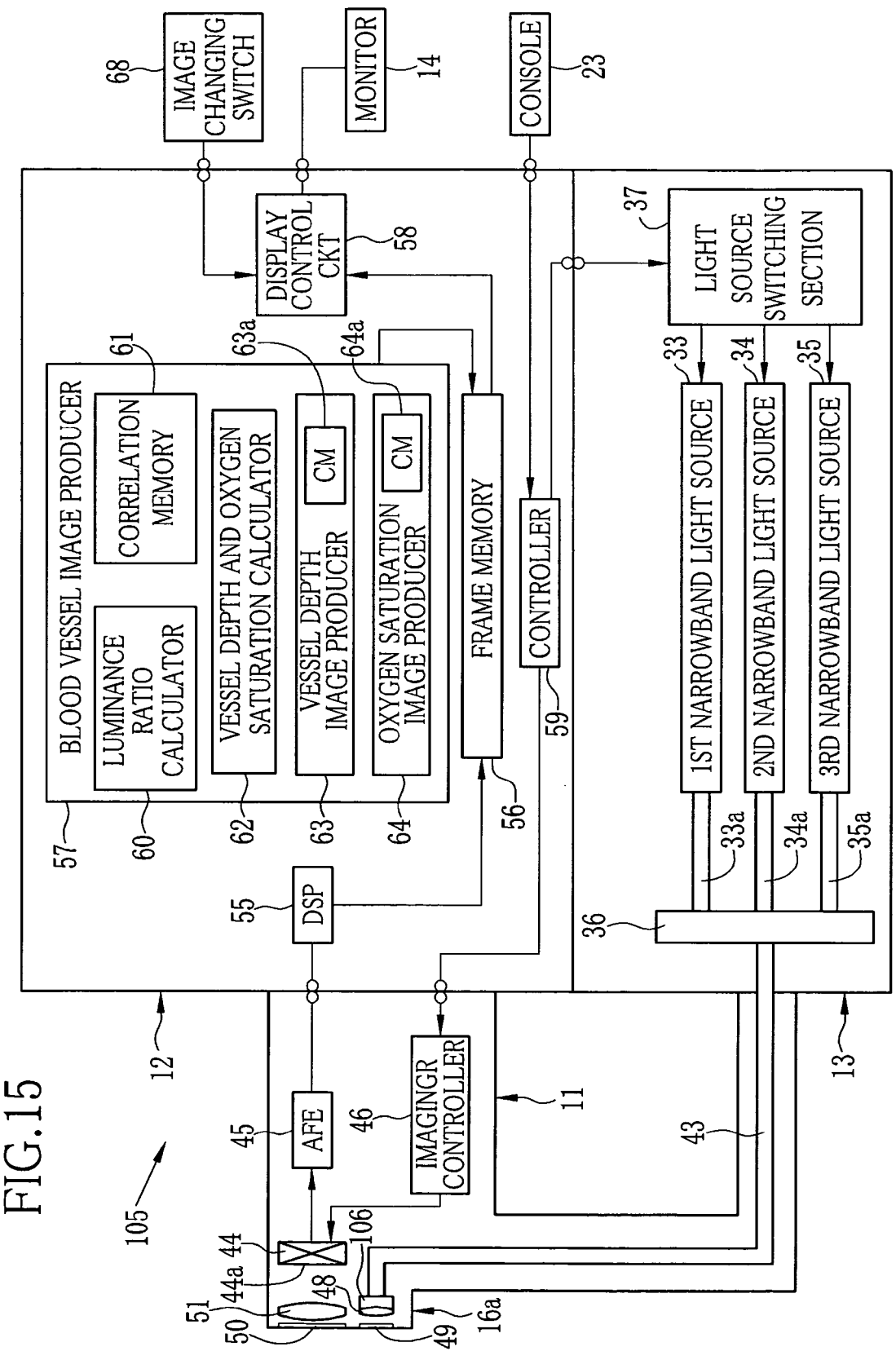
FIG. 15 is a block diagram illustrating the circuitry of an electronic endoscope system according to a fifth embodiment of the present invention.

Referring to FIG. 15, an electronic endoscope system 105 of the fifth embodiment of the present invention is shown, wherein the broadband light source 30 is not provided, but a fluorescent material 106 is provided at an outlet port of a light guide 43, so that the fluorescent material 106 generates the broadband light BB from the first to third narrowband rays N1 to N3. Otherwise, the fifth embodiment may have the same configuration as the electronic endoscope system 10 of the first embodiment. Therefore, merely essential features of the fifth embodiment will be described.

The fluorescent material 106 converts one fractions of the first to third narrowband rays N1 to N3 to broadband light BB having a wavelength range from about 470 to 700 nm, and also let other fractions of the first to third narrowband rays N1 to N3 pass through it without any conversion. In the fifth embodiment, the first to third narrowband rays N1 to N3 are projected in the following sequence, to obtain the same image signals as in the third embodiment.

First, the first narrowband light source 33 is turned ON. Then, the body cavity is illuminated with the broadband light BB obtained from the first narrowband ray N1 by the conversion through the fluorescent material 106 as well as the first narrowband ray N1 passing through the fluorescent material 106 without conversion. When an image frame is captured under this lighting condition is complete, the first narrowband light source 33 is turned OFF, and the second and third narrowband light sources 34 and 35 are turned ON. Then, the body cavity is illuminated with the broadband light BB obtained from the second and third narrowband rays N2 and N3 by the conversion through the fluorescent material 106 as well as the second and third narrowband rays N2 and N3 passing through the fluorescent material 106 without conversion. Another image frame is captured under this lighting condition. These two frames of image signal are converted to the first to third narrowband image data in the same sequence as the third embodiment.

The above first to fifth embodiments use the first to third narrowband light sources for the purpose of obtaining the blood vessel depth and the oxygen saturation. It is possible to use a fourth narrowband light source in addition to these light sources. The fourth narrowband light source may generate a fourth narrowband ray N4 having a limited wavelength of around 532 nm (for example 530±10 nm). The first to fourth narrowband ray N1 to N4 are projected to obtain the first to fourth narrowband image data, based on which the blood vessel depth and the oxygen saturation may be determined. Since the light of longer wavelength will reach deeper inside the subject tissues, the fourth narrowband ray N4 having the longer wavelength than the second narrowband ray N2 will provide information about those blood vessels which exit in a deeper range than the second narrowband ray N2 can reach.

In this configuration, the luminance ratio calculator 60 extracts the vascular area from the first to fourth narrowband image data. Then, like the first embodiment, the first and second luminance ratios S1/S3 and S2/S3 are determined. In addition, the luminance ratio calculator determines a third luminance ratio S4/S3 between the third narrowband image data and the fourth narrowband image data, wherein S4 represents pixel luminance of the fourth narrowband image data. Thereafter, in the same procedure as the first embodiment, the vessel depth and oxygen saturation calculator 62 acquires information on the blood vessel depth and the oxygen saturation corresponding to the first to third luminance ratios calculated by the luminance ratio calculator 60, with reference to correlation between the first to third luminance ratios S1/S3, S2/S3 and S4/S3 and the blood vessel depth and the oxygen saturation, the correlation being previously experimentally obtainable.

The first to fourth narrowband rays N1 to N4 may be individually projected into the body cavity, or it is possible to project any two or more of the first to fourth narrowband rays N1 to N4 as a composite light, like in the second or the third embodiment, in order to reduce the number of image frames to be correlated. For example, the first narrowband ray N1 and the fourth narrowband ray N4 may be simultaneously projected into the body cavity to capture a first image frame. Thereafter, the second narrowband ray N2 and the third narrowband ray N3 may be projected simultaneously into the body cavity to capture a second image frame.

The first image frame includes a blue image signal B1 and a green image signal G1, whereas the second image frame includes a blue image signal B2 and a green image signal G2. These image signals B1, G1, B2 and G2 have the following luminance values:

Image signal $B1$=luminance $L1$ based on the first narrowband ray $N1$+luminance $L4$ based on the fourth narrowband ray $N4$ Image signal G1=luminance $L4$ based on the fourth narrowband ray N4

Image signal $B2$=luminance $L2$ based on the second narrowband ray $N2$+luminance $L3$ based on the third narrowband ray $N3$ Image signal G2=luminance L2 based on the second narrowband ray N2

From the image signal G2 having the luminance L2 only, the second narrowband image data may be produced. From the image signal G1 having the luminance L4 only, the fourth narrowband image data may be produced. With the calculation: B1−(constant)×G1, the luminance L4 may be separated from the image signal B1, to produce the first narrowband image data, wherein the constant is decided by the intensity ratio between the first narrowband ray N1 and the fourth narrowband ray N4. With the calculation: B2−(constant)×G2, the luminance L3 may be separated from the image signal B2, to produce the second narrowband image data, wherein the constant is decided by the intensity ratio between the second narrowband ray N2 and the third narrowband ray N3.

Figure 16:
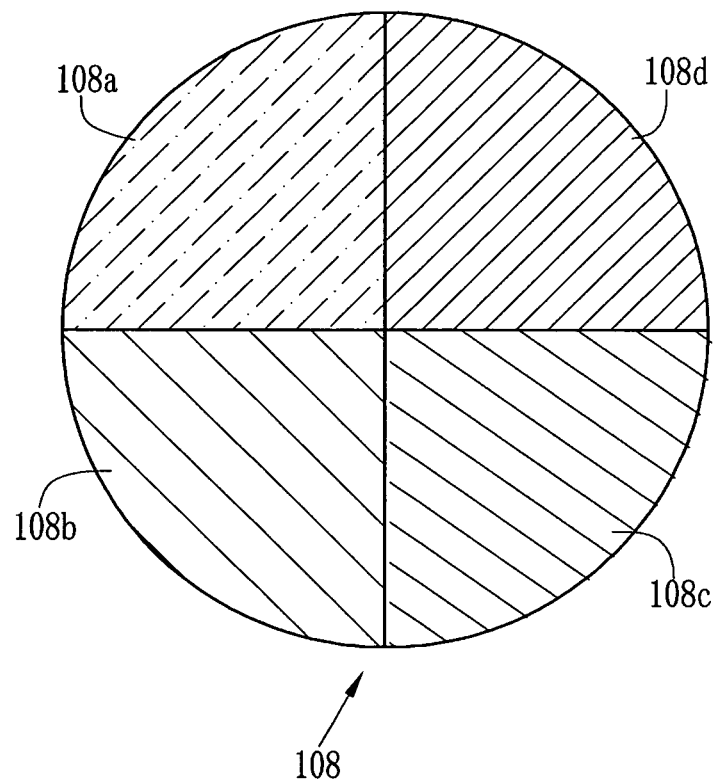
FIG. 16 is a schematic diagram illustrating a rotary filter.

In the first to third embodiments, the first to third narrowband light sources are used for generating the first to third narrowband rays N1 to N3. In another embodiment, the first to third narrowband light sources are not installed, but a rotary filter 108 is installed in place of the shutter 31 of FIG. 2, so that the first to third narrowband rays N1 to N3 may be generated from the broadband light BB through the rotary filter 108. As shown in FIG. 16, the rotary filter 108 includes a broadband light transmissive sector 108a that allows the whole broadband light BB from the broadband light source 30 to pass through it. The rotary filter 108 also includes first to third narrowband light transmissive sectors 108b, 108c and 108d. The first narrowband light transmissive sector 108b allows merely the first narrowband ray N1 to pass through it among the light components of the broadband light BB. The second narrowband light transmissive sector 108c allows merely the second narrowband ray N2 of the broadband light BB to pass through it. The third narrowband light transmissive sector 108d allows only the third narrowband ray N3 of the broadband light BB to pass through it. The rotary filter 108 is rotatable such that the broadband light transmissive sector 108a is placed on the optical path of the broadband light source 30 to generate the broadband light BB, or the first, the second or the third narrowband light transmissive sector 108b, 108c or 108d is placed on the optical path of the broadband light source 30 to generate the first, the second or the third narrowband ray N1, N2 or N3, respectively.

Figure 17A:
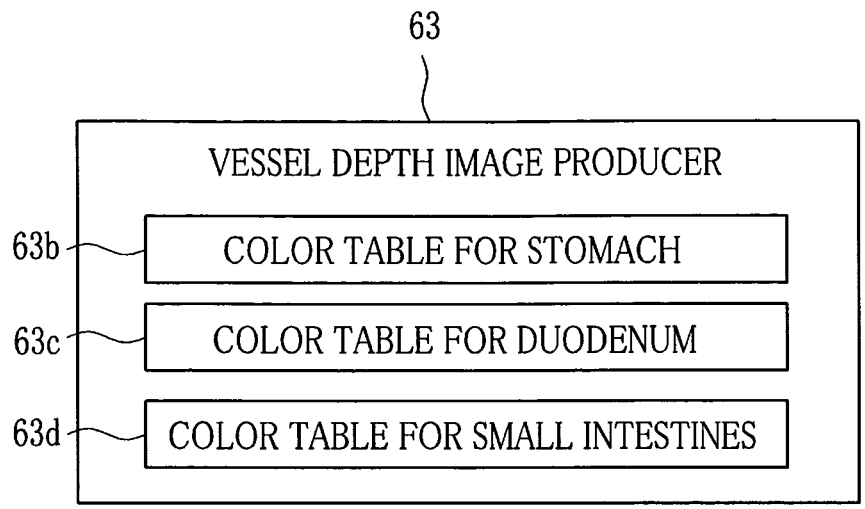
FIG. 17A is an example of a block diagram illustrating a vessel depth image producer.

In another embodiment, the vessel depth image producer 63 may include multiple color tables specified for different body sites. As shown for example in FIG. 17A, the vessel depth image producer 63 may include a color table 63b for stomach, a color table 63c for duodenum, and a color table 63d for small intestines. From among these color tables 63b to 63d, the operator can select a suitable one by operating the console 23 in accordance with the subject tissues under inspection. The color table 63b for stomach stores color information corresponding to blood vessel depth ranges in the stomach. The color table 63c for duodenum stores color information corresponding to blood vessel depth ranges in the duodenum, and the color table 63d for small intestines stores color information corresponding to blood vessel depth ranges in the small intestines. The vessel depth image producer 63 uses one of the color tables 63b to 63d, which is selected at the console 23, to determine a color to be assigned to the blood vessel depth U* that is calculated by the vessel depth and oxygen saturation calculator 62 in the way as described above. Note that the color tables are not limited to those for stomach, duodenum and small intestines, but other color tables may be used in addition to or instead of these color tables.

Figure 17B:
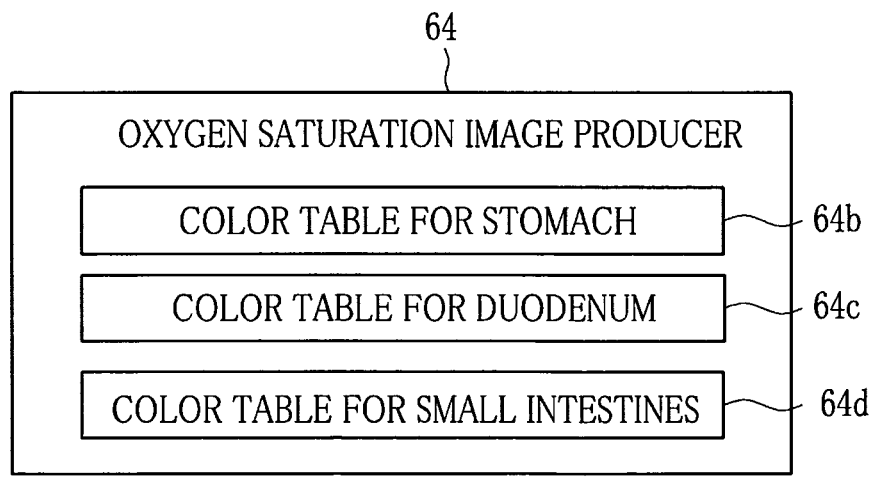
FIG. 17B is a block diagram illustrating an example of an oxygen saturation image producer.

Like the vessel depth image producer 63, the oxygen saturation image producer 64 may also include multiple color tables for different body sites. For example, as shown in FIG. 17B, the oxygen saturation image producer 64 may include a color table 64b for stomach, a color table 64c for duodenum, and a color table 64d for small intestines. These color tables 64b to 64d are selectable by operating the console 23. The oxygen saturation image producer 64 uses either of the color tables 64b to 64d, which is selected at the console 23, to determine a color to be assigned to the oxygen saturation V* that is calculated by the vessel depth and oxygen saturation calculator 62.

Figure 18:
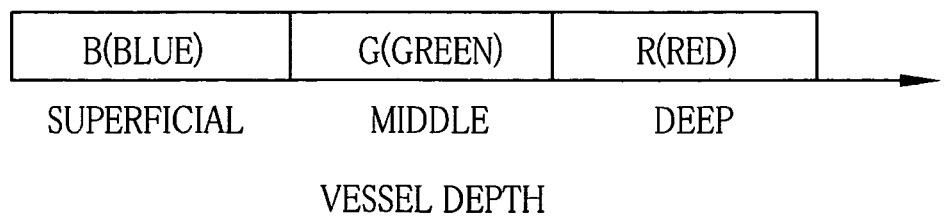
FIG. 18 is a graph showing color information that represents the blood vessel depth in three grades.

The color tables 63b to 63d of the vessel depth image producer 63 may store color information that allocates different colors to different grades of the blood vessel depth. In an example, as shown in FIG. 18, the blood vessel depth is graded into a superficial range, a middle range, and a deep range, and as the color information, blue represents blood vessels in the superficial range, green represents blood vessels in the middle range, and red represents blood vessels in the deep range. Likewise, color information representative of the oxygen saturation may allocate different colors to different oxygen saturation levels. In the above described first embodiment, cyan represents a low oxygen saturation level, magenta represents a middle oxygen saturation level, and yellow represents a high oxygen saturation level. But the color information is not limited to this embodiment. For example, yellow may be assigned to oxygen saturation of 0% to 30%, magenta to oxygen saturation of 30% to 70%, and so forth.

In another embodiment, a half color circle between two complementary colors, for example, hues from red (R) to cyan (Cy) may be used for the color information stored in the color tables 63b to 63d of the vessel depth image producer. In the color information shown in FIG. 19A, red (R) represents a superficial range of the blood vessel depth, and the hue changes from red (R) to yellow (Ye), green (G), and cyan (Cy) as the blood vessel depth increases. Color information stored in the color tables 64b to 64d of the oxygen saturation image producer 64 may also be a half color circle between two complementary colors. In an example of FIG. 19B, the color information is cyan (Cy) for a lowest oxygen saturation level, and the hue changes from cyan to blue (B), magenta (M) and red (R) with an increase in the oxygen saturation. The color circles used for representing the blood vessel depth and the oxygen saturation level may be interchanged. For example, the color circle from red to cyan may serve as the color information on the oxygen saturation, while the color circle from cyan to red may serve as the color information on the blood vessel depth. Moreover, it is possible to use the same pattern or sequence of colors, such as hues from R to Cy, for both the oxygen saturation and the blood vessel depth, except in a case where the oxygen saturation and the blood vessel depth are indicated as color information within the same vascular image or an image of a single blood vessel, as will be described later.

Figure 20A:
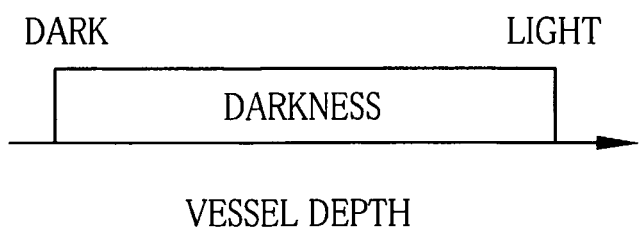
FIG. 20A is a graph showing a gray scale indicative of the blood vessel depth.

In another embodiment, as shown in FIG. 20A, a gray scale or lightness gradation of an achromatic or chromatic color may serve as the color information. In the example of FIG. 20A, the darkness decreases (the lightness increases) as the blood vessel depth increases.

Figure 20B:
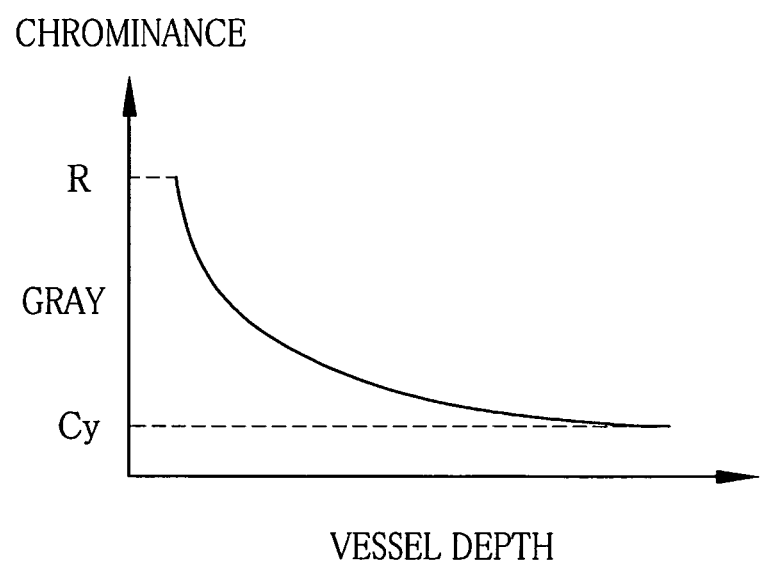
FIG. 20B is a graph showing a gradation between two colors, served as a scale for the blood vessel depth.

It is also possible to use a gradation between two complementary colors for the color information, as shown in FIG. 20B. For example, as the color information, the chrominance changes from red to cyan with the increase in the blood vessel depth. As the gradation between two complementary colors includes neutral in the intermediate point, blood vessels in the middle depth range will be displayed in gray. According to a result of experiments, the gradation between two complementary colors is effective to improve the visibility of the subsequent vascular image. The same gradation scale as shown in FIG. 20A or 20B may be applied to the color information for the oxygen saturation.

Figure 19A:
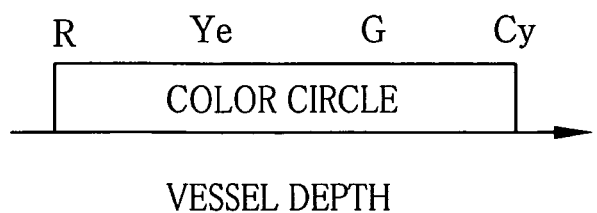
FIG. 19A is a graph showing a half color circle between two complementary colors, served as a scale for the blood vessel depth.
Figure 19B:
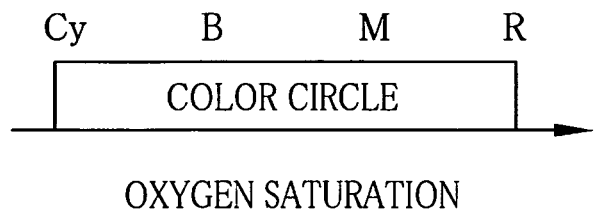
FIG. 19B is a graph showing a half color circle between two complementary colors, served as a scale for the oxygen saturation.

Although the same kind of color information is applied to the blood vessel depth and the oxygen saturation in the above embodiments, different kinds of color information may represent different vascular information. For example, while the color information representing the blood vessel depth is a half color circle containing hues between two complementary colors, like as shown in FIG. 19A, the color information representing the oxygen saturation may be a gray scale, a lightness gradation of a chromatic color, or a gradation between two complementary colors, like as shown in FIG. 20, instead of a half color circle containing hues between two complementary colors, like as shown in FIG. 19B.

After deciding the color information to every pixel inside the vascular area, the vessel depth image producer 63 reads out the broadband image data from the frame memory 56, to reflect the color information on the broadband light image data. Thus, data of a vessel depth image is produced, which informs of the depth levels of the contained blood vessels. The vessel depth image data is stored in the frame memory 56. Alternatively, the color information may be reflected on either of the first to third narrowband image data or a composite image composed of the first to third narrowband image data, not on the broadband light image data. It is also possible to convert the broadband image data to an achromatic image to reflect the color information on the vascular area in the achromatic image. Reflecting the color information on the first to third narrowband image data or on the monochrome image will improve the visibility of the vascular information.

Like the vessel depth image producer 63, the oxygen saturation image producer 64 reflects the color information on the broadband image data with respect to every pixel in the vascular area, to produce data of an oxygen saturation image. The oxygen saturation image data is stored in the frame memory 56, like the vessel depth image data.

On the basis of the image data stored in the frame memory 56, the display control circuit 58 displays images on the monitor 14. For example, as shown in FIG. 21, the monitor 14 displays an image 72 based on the broadband image data on one side of a screen, as well as a vessel depth image 73 based on the vessel depth image data and an oxygen saturation image 74 based on the oxygen saturation image data on the other side of the screen. For example, where the color information stored in the color tables 63b to 63d and 64b to 64d correspond to the color circles shown in FIGS. 19A and 19B, the vessel depth image 73 contains vascular image 75 of superficial blood vessels that is displayed in red (R), vascular image 76 of middle-layer vessels displayed in green (G), and vascular image 77 of deep blood vessels displayed in cyan (Cy). On the other hand, in the oxygen saturation image 74, vascular image 80 of low oxygen saturation is displayed in cyan (Cy), vascular image 81 of middle oxygen saturation is displayed in magenta (M), and vascular image 82 of high oxygen saturation is displayed in red (R).

In addition, the vessel depth image 73 contains a color bar 73a showing hues from red to cyan of the color circle, and the oxygen saturation image 74 contains a color bar 74a showing hues from cyan to red of the color circle. The color bar 73a has an arrow to show the direction in which the blood vessel depth increases, with text information about the vessel depth on opposite ends of the arrow. The color bar 74a also has an arrow and text information in the same manner as the color bar 73a. Displaying the color bars 73a and 74a with the vessel depth image 73 and the oxygen saturation image 74 will help visual recognition of the relation between the color information reflected on the vessel depth image 73 and the blood vessel depth, as well as the relation between the color information reflected on the oxygen saturation image 74 and the oxygen saturation.

Figure 22:
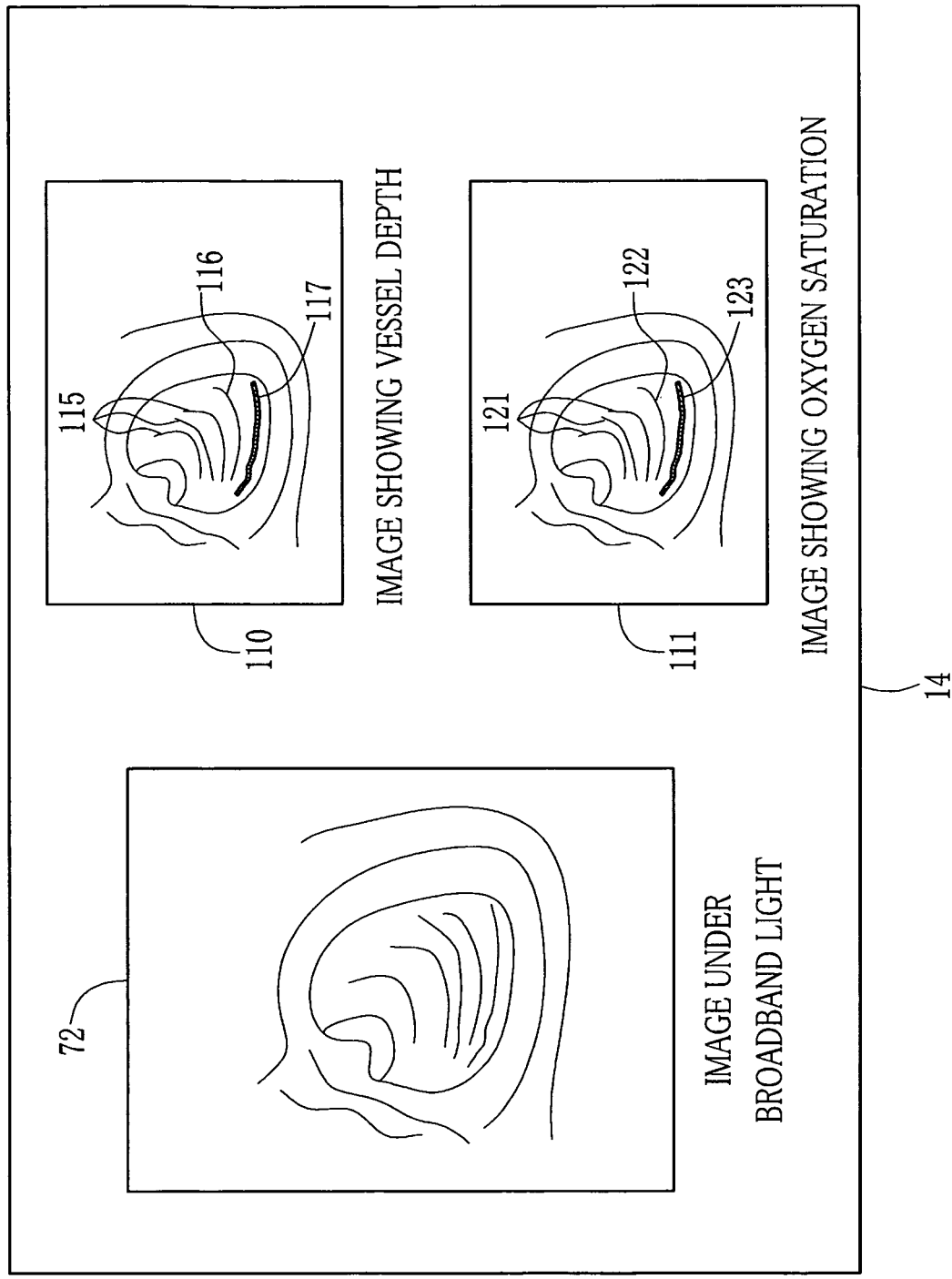
FIG. 22 is a diagram illustrating a monitor screen displaying an image showing information on the vessel depth and an image showing information on the oxygen saturation, wherein vessels in a designated depth range or at a designated oxygen saturation level are emphasized.

In the embodiment of FIG. 21, the colors of the vascular images 75 to 77 in the vessel depth image 73 change depending on the blood vessel depth, and the colors of the vascular images 80 to 82 in the oxygen saturation image 74 change depending on the oxygen saturation. In another embodiment, as shown in FIG. 22, a vessel depth image 110 may emphasize such vascular image 117 that represents blood vessels in a deeper range than a predetermined level among other vascular images 115 and 116 representative of blood vessels in a shallower range. Also in an oxygen saturation image 111, vascular image 123 representative of those blood vessels in which oxygen saturation is more than a predetermined level among other vascular images 121 and 122.

Figure 23:
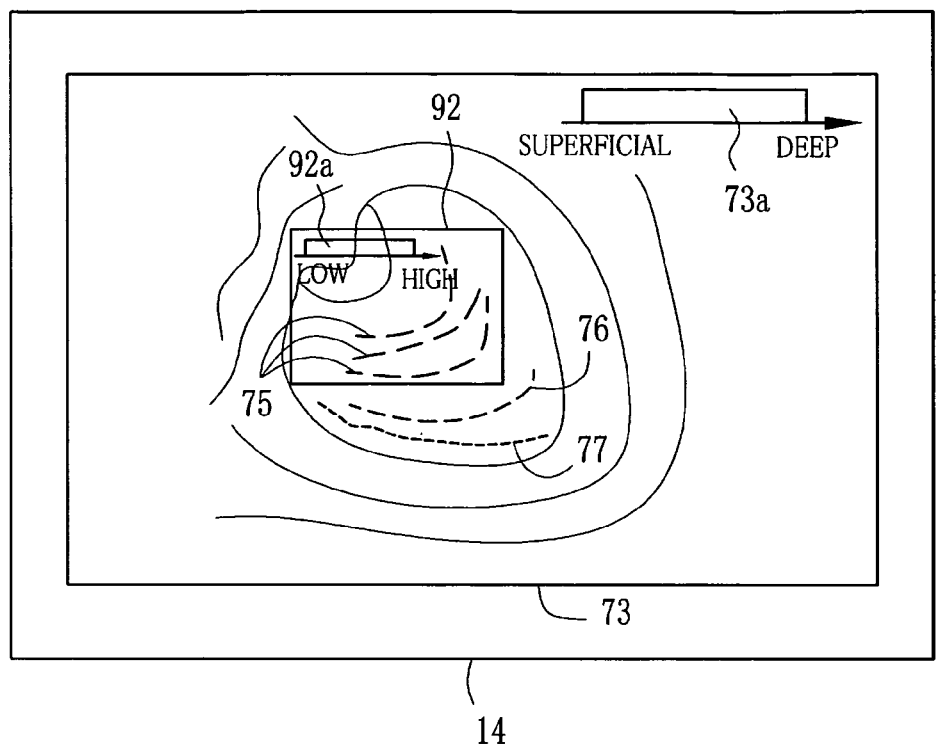
FIG. 23 is a diagram illustrating an example of an image displayed on a monitor, wherein an image showing the vessel depth includes a section reflecting the oxygen saturation.

In the above embodiments, the blood vessel depth and the oxygen saturation are respectively shown as color information in the vessel depth image 73 and the oxygen saturation image 74. Alternatively, it is possible to reflect these two kinds of vascular information as color information on a single image. For example, as shown in FIG. 23, among vascular images 75 to 77 contained in a vessel depth image 73, the vascular images 76 and 77 may be displayed in such colors or gradations that represent the blood vessel depth (for example, using the color circle between two complementary colors), whereas vascular image 75 inside a designated section 92 may be displayed in such colors or gradations that does not represent the blood vessel depth but the oxygen saturation. Thus, it is possible to display two kinds of vascular information in one endoscopic image.

The designated section 92 is displayed in a way distinguishable from other portions of the image 73, for example, by changing the background color or framing with a frame. On the upper left corner of the designated section 92 is displayed a color bar 92a corresponding to the color information about the oxygen saturation. The designated section 92 may be located anywhere in the vessel depth image 73, by operating the console 23, or may be located in a predetermined portion of the image 73. This embodiment allows checking the oxygen saturation of blood vessels in the designated section 92 of the vessel depth image 73, while checking the depth of blood vessels in other portions of the vessel depth image 73.

Figure 24:
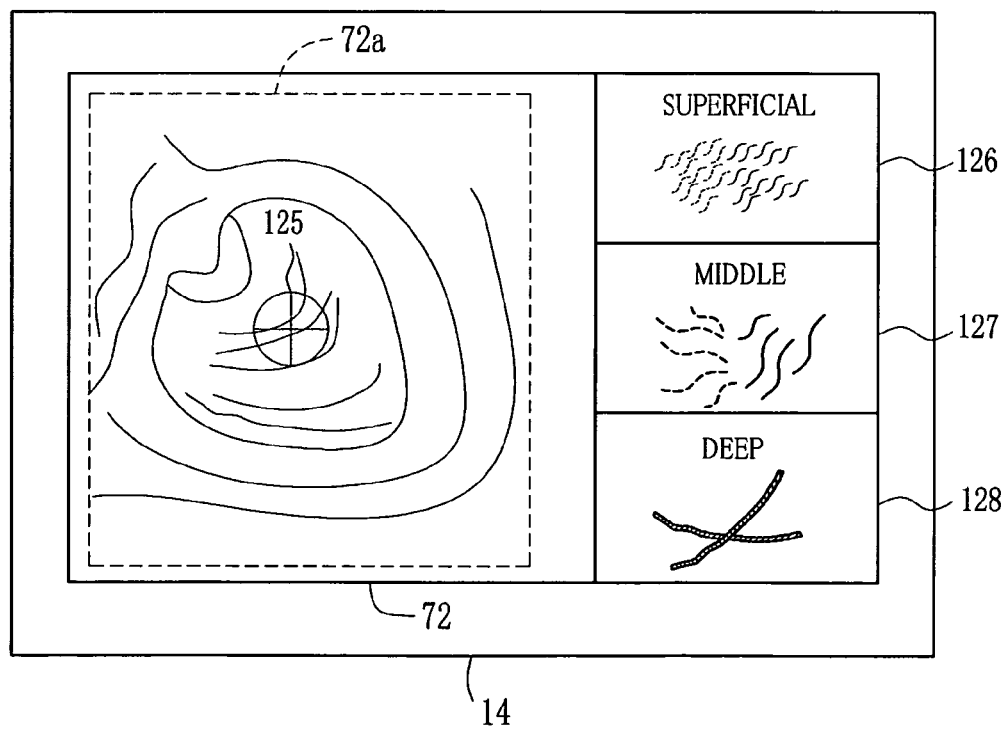
FIG. 24 is a diagram illustrating an embodiment, wherein blood vessels existing in a designated portion of an image taken under broadband light are displayed separately according to their depths.

Alternatively, as shown in FIG. 24, a section 125 may be designated in the broadband light image 72, so that images of blood vessels in the designated section 125 are displayed separately from an image display area 72a for the broadband light image 72. Moreover, an image 126 of superficial blood vessels, an image 127 of middle-layer vessels, and an image 128 of deep blood vessels are displayed in an enlarged size, separately from each other. Furthermore, color information about the oxygen saturation is reflected on the respective vascular images 126 to 128. For example, in each vascular image shown in FIG. 24, dashed lines show the vessels of low oxygen saturation, solid lines show the vessels of high oxygen saturation. In the same way as described above, it is possible to display an image of blood vessels at a low oxygen saturation level, an image of blood vessels at a middle oxygen saturation level, and an image of blood vessels at a high oxygen saturation level in an enlarged size, separately from the broadband light image 72 as well as from each other. In that case, color information about the blood vessel depth may be reflected on the respective vascular images as sorted according to the oxygen saturation. In addition to the color information, it is possible to display text information in the respective vascular images: the text information may be a numerical value of the blood vessel depth, an average oxygen saturation of the vessels contained in each vascular image, the area size of those vessels at the low oxygen saturation level, the area size of those vessels at the high oxygen saturation level, and so forth.

Figure 25:
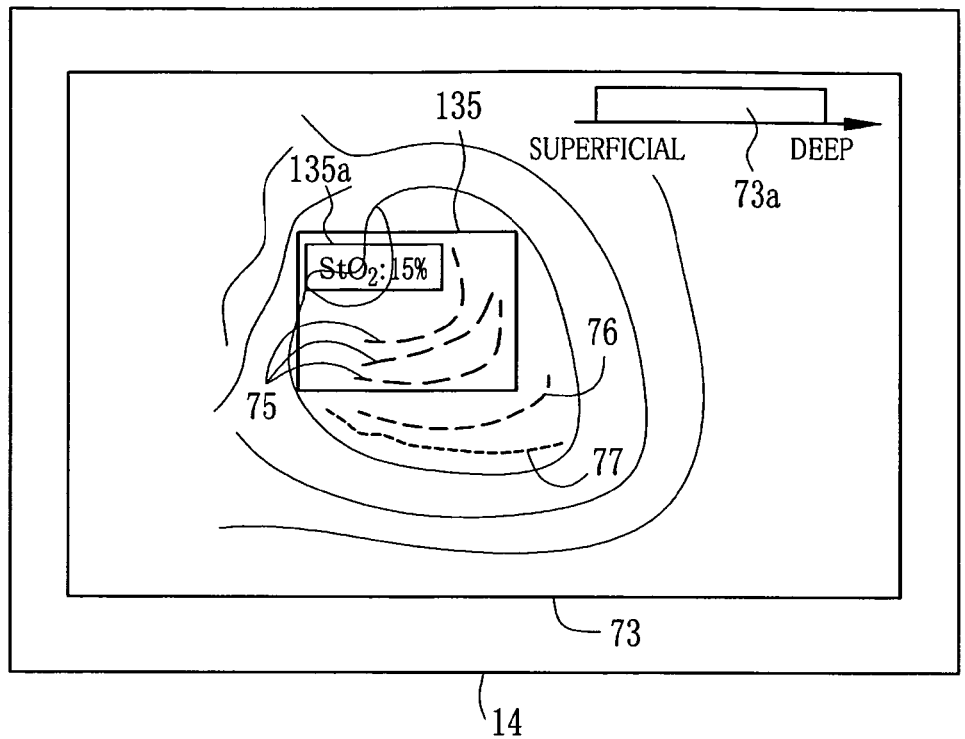
FIG. 25 is an explanatory diagram illustrating an embodiment, wherein a section containing those blood vessels having a given oxygen saturation level or being in a given oxygen saturation range is automatically outlined within an image showing information on the vessel depth.

In the embodiment of FIG. 23, the location of the section 92 in the vessel depth image 73 is designated by operating the console 23. In another embodiment, as shown in FIG. 25, an operator may enter an oxygen saturation level or range through the console 23 before or while the operator is making diagnosis based on an endoscopic image 72. Then, a section containing those vessels which are at the entered oxygen saturation level or in the entered oxygen saturation range is automatically surrounded by a bounding frame 135. A numerical value 135a indicating the oxygen saturation level or range may also be displayed inside the frame 135.

Figure 26:
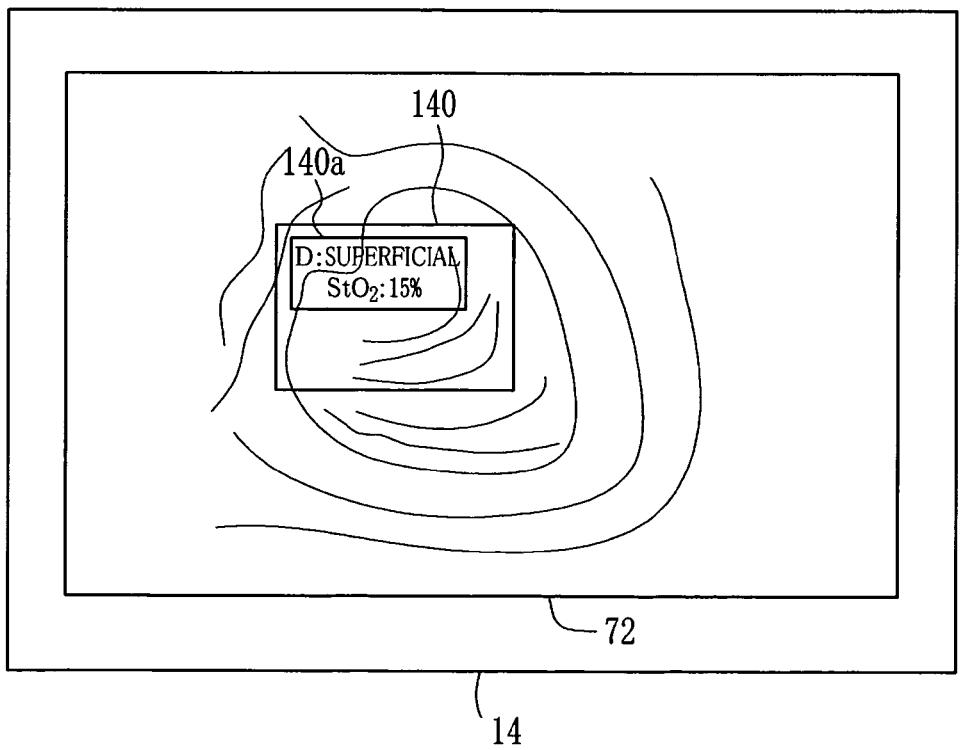
FIG. 26 is an explanatory diagram illustrating an embodiment, wherein a frame is automatically displayed on an endoscopic image to surround those blood vessels having a given oxygen saturation level or being in a given oxygen saturation range and existing at a given depth or in a given depth range.

In the embodiment of FIG. 25, the frame 135 is displayed in the vessel depth image 73 to surround those blood vessels having a given oxygen saturation level or being in a given oxygen saturation range. Alternatively, as shown in FIG. 26, a bounding frame 140 may be automatically displayed in a broadband light image 72, to surround those blood vessels having a given oxygen saturation level or being in a given oxygen saturation range and existing at a given depth or in a given depth range. Numerical values 140a indicating the oxygen saturation (StO2) and the blood vessel depth (D) may be displayed inside the frame 140.

Figure 27:
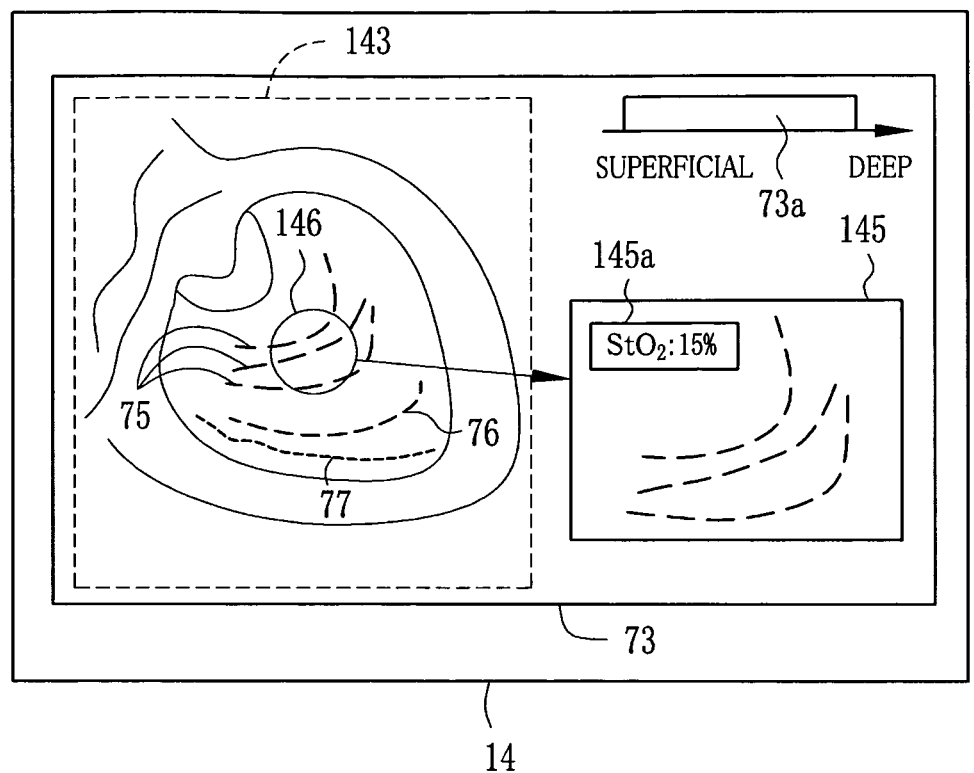
FIG. 27 is an explanatory diagram illustrating an embodiment, wherein a window showing blood vessels at a given oxygen saturation level or in a given oxygen saturation range is displayed outside an endoscopic image.

In another embodiment, as shown in FIG. 27, a window 145 may be displayed outside an endoscopic image 143, showing those vessels having such oxygen saturation levels that are more than a given value or in a given range. A numerical value 145a indicating the oxygen saturation of the vessels shown in the window 145 is displayed in a corner of the window 145. On the other hand, in the endoscopic image 143, a circle 146 roughly shows the original location of the vessels displayed in the window 145. Thus, the circle 146 in the image 143 provides a linkage or shows the correlation between the vessels in the window 145 and the vessels in the endoscopic image 143. Although the embodiment of FIG. 27 has been described with respect to a vessel depth image 73, it is possible to display a separate window with respect to an oxygen saturation image 74 in the same way as for the vessel depth image 73.

It is also possible to provide two sections in a broadband light image: one reflecting color information about the blood vessel depth, and the other reflecting color information about the oxygen saturation.

Figure 28:
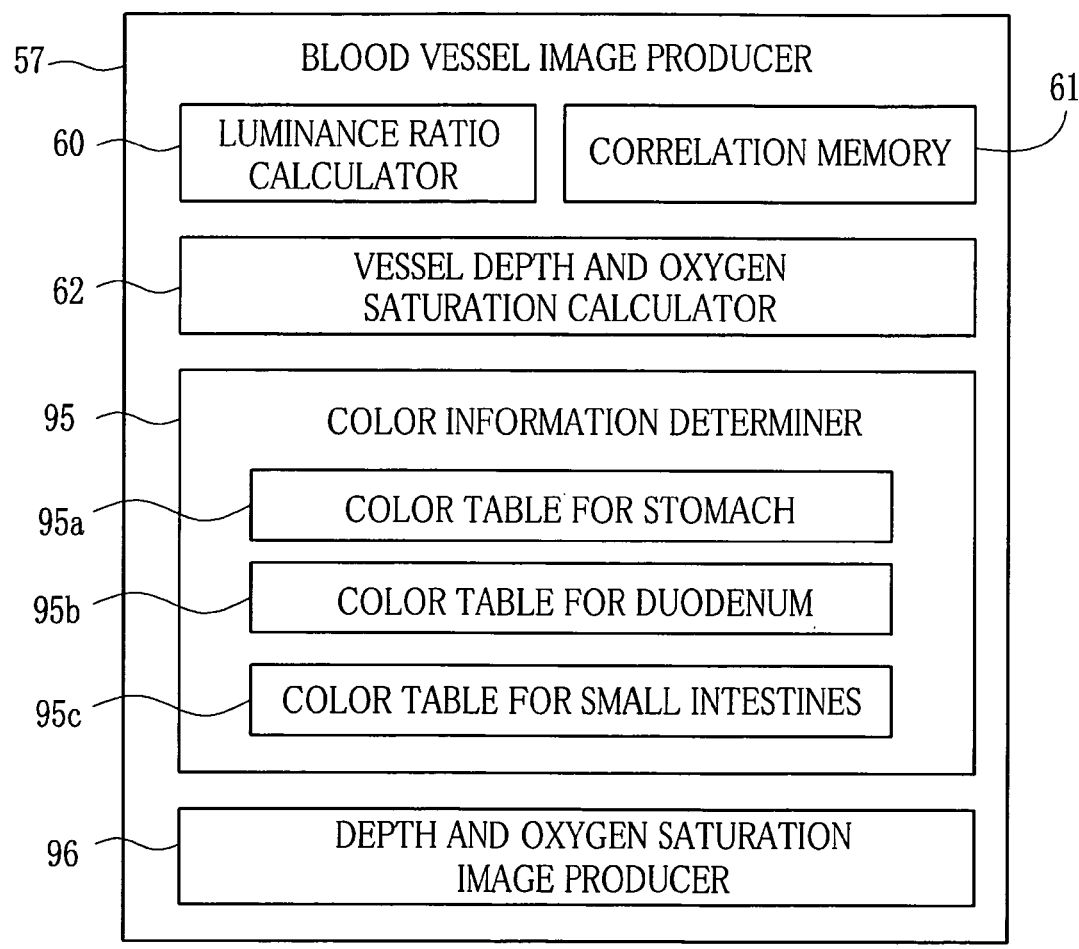
FIG. 28 is a block diagram illustrating another structure of a blood vessel image producer according to a further embodiment of the present invention.

In a further embodiment, as shown in FIG. 28, a blood vessel image producer 57 does not include the vessel depth image producer 63 and the oxygen saturation image producer 64, but includes a color information determiner 95 and a vessel depth and oxygen saturation image producer 96 instead. The color information determiner 95 determines color information that corresponds to both the blood vessel depth and the oxygen saturation.

Figure 29:
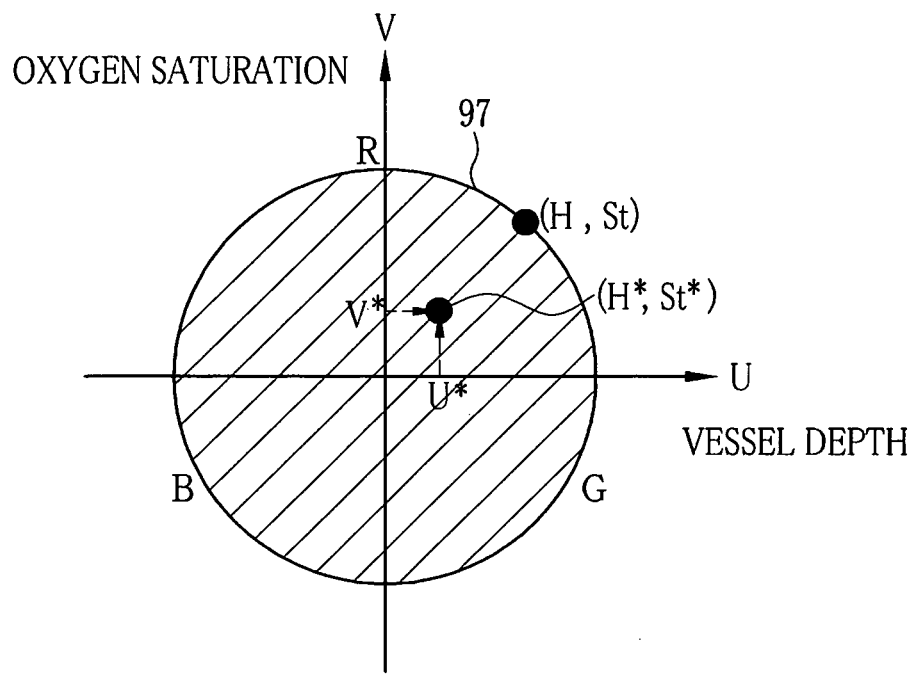
FIG. 29 is a graph showing a U-V coordinate system that is associated with a color circle.

The color information determiner 95 includes a color table 95a for stomach, a color table 95b for duodenum, and a color table 95c for small intestines. In the color tables 95a to 95c, a color circle 97 is associated with a U-V coordinate system, of which U axis represents the blood vessel depth and V axis represents the oxygen saturation, as shown in FIG. 29, whereby color information is stored in association with the blood vessel depth and the oxygen saturation. The circumferential direction of the color circle 97 represents hues H, and the radial direction of the color circle 97 represents color saturation St. The color information determiner 95 refers to a suitable one of the color tables 95a to 95c according to the body site being inspected, thereby to determine the hue H* and the color saturation St* corresponding to the blood vessel depth U* and the oxygen saturation V*, which may be calculated by the vessel depth and oxygen saturation calculator 62 in the same way as described above.

Figure 30:
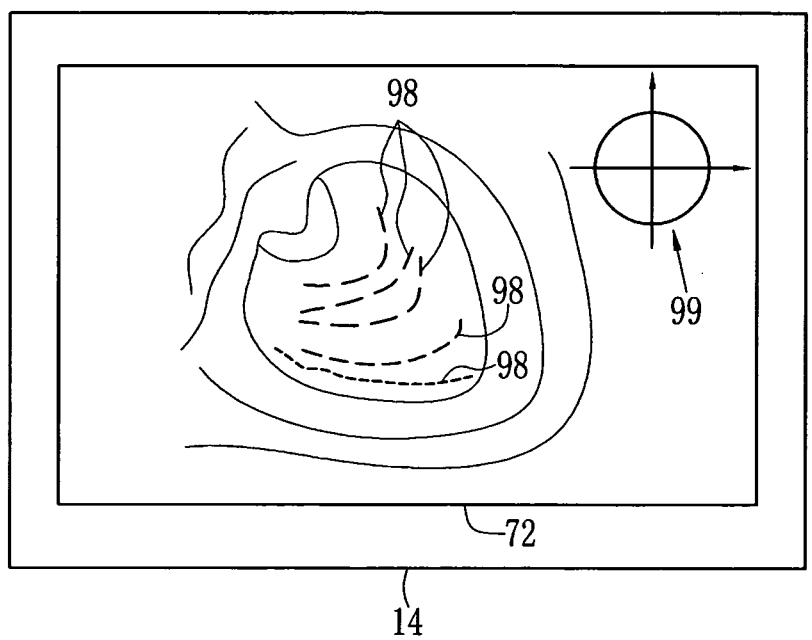
FIG. 30 is a diagram illustrating an image taken under broadband light, on which color information is reflected, wherein one color is assigned to each combination of the blood vessel depth and the oxygen saturation.

When the color information representative of the hue and the color saturation has been determined with respect to every pixel in the vascular area, the vessel depth and oxygen saturation image producer 96 reflects the determined color information on broadband image data that is read out from the frame memory 56. Based on the broadband image data output from the vessel depth and oxygen saturation image producer 96, on which the color information about the blood vessel depth and the oxygen saturation is reflected, the display control circuit 58 controls the monitor 14 to display a broadband light image 72, as shown in FIG. 30. The broadband light image 72 of this embodiment contains vascular images 98 having variable hues, and color saturations according to the blood vessel depth and the oxygen saturation. In addition, a scale 99 indicating the color circle associated with the U-V coordinate system is displayed on the same screen as the broadband light image 72, to show the relation between the color information and the vessel depth and the oxygen saturation.

Figure 31:
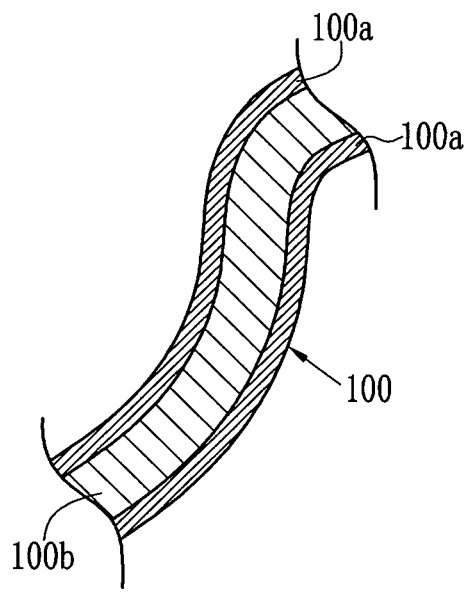
FIG. 31 is a diagram illustrating an example of an image displayed on a monitor, wherein an individual blood vessel is displayed in such colors that reflect the blood vessel depth and the oxygen saturation of that vessel.

In another embodiment of the present invention, an individual vascular image may be displayed in two colors in an endoscopic image: one is color information reflecting the blood vessel depth, and the other is color information reflecting the oxygen saturation. For example, as shown in FIG. 31, edges 100a along an axis of a blood vessel 100 are displayed in a color designated as color information about the blood vessel depth, whereas a center area 100b along the axis of the blood vessel 100 is displayed in another color designated as color information about the oxygen saturation. The endoscopic image containing such dual-colored vascular images may be a broadband light image or an achromatic image. The color information applied to this embodiment may be based on the color circle. For example, the hues from red to cyan are usable for the blood vessel depth, and the hues from cyan to red are usable for the oxygen saturation, like the embodiment of FIG. 19. The color information based on the gradation between two complementary colors or the neutral gradation is also applicable to this embodiment.

Figure 32:
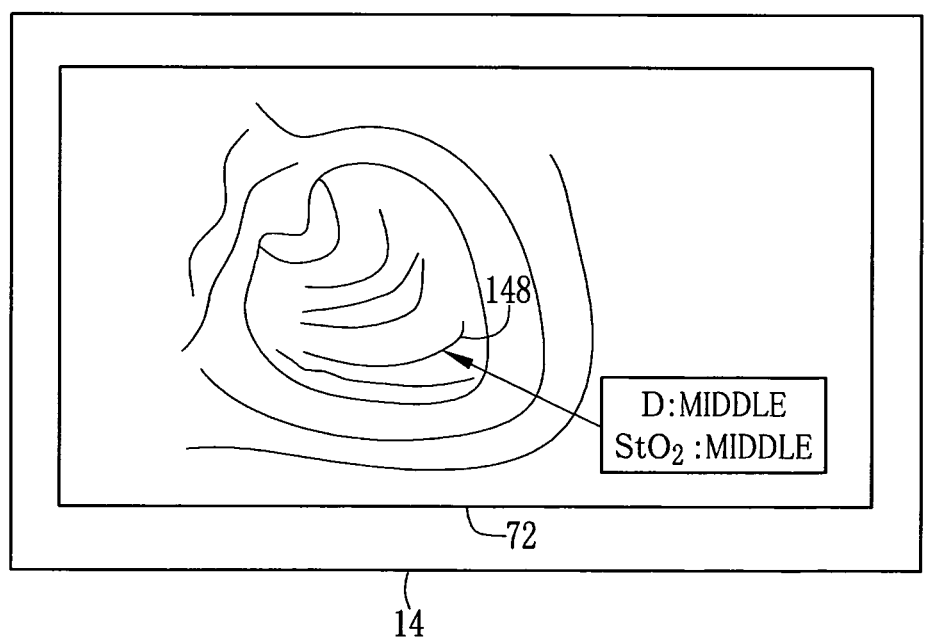
FIG. 32 is a diagram illustrating an image displayed on a monitor, wherein the blood vessel depth and the oxygen saturation are displayed as text information.

Referring to FIG. 32 illustrating another embodiment of the present invention, it is possible to display text information about the blood vessel depth (D) and the oxygen saturation (StO2) of a designated vessel 148 in a broadband light image 72. Designation of the vessel may be carried out by operating the console 23. Instead of the text information, vascular information may be displayed as a vector, of which the length represents the blood vessel depth, and the angle represents the oxygen saturation.

According to another embodiment of the present invention, color information representative of the oxygen saturation is reflected only on those vessels which are in a designated depth range. In an example shown in FIG. 33, vascular images 157 of superficial blood vessels are distinguished from other vascular images 158 and 159 in the broadband light image 72. For example, merely the vascular images 157 of superficial blood vessels are colored with variable hues according to their oxygen saturation levels. The color information may for example be based on the hues from cyan to red of the color circle, wherein vessels of the low oxygen saturation is displayed in cyan, and vessels of the high oxygen saturation are displayed in red. A color bar 72b showing the color information as a scale for the oxygen saturation is displayed in the broadband light image 72. Although the color information about the oxygen saturation is reflected on the vascular images of superficial vessels in the above example, it is alternatively possible to reflect the color information about the oxygen saturation on vascular images of middle-layer vessels or on vascular images of deep blood vessels.

Figure 33:
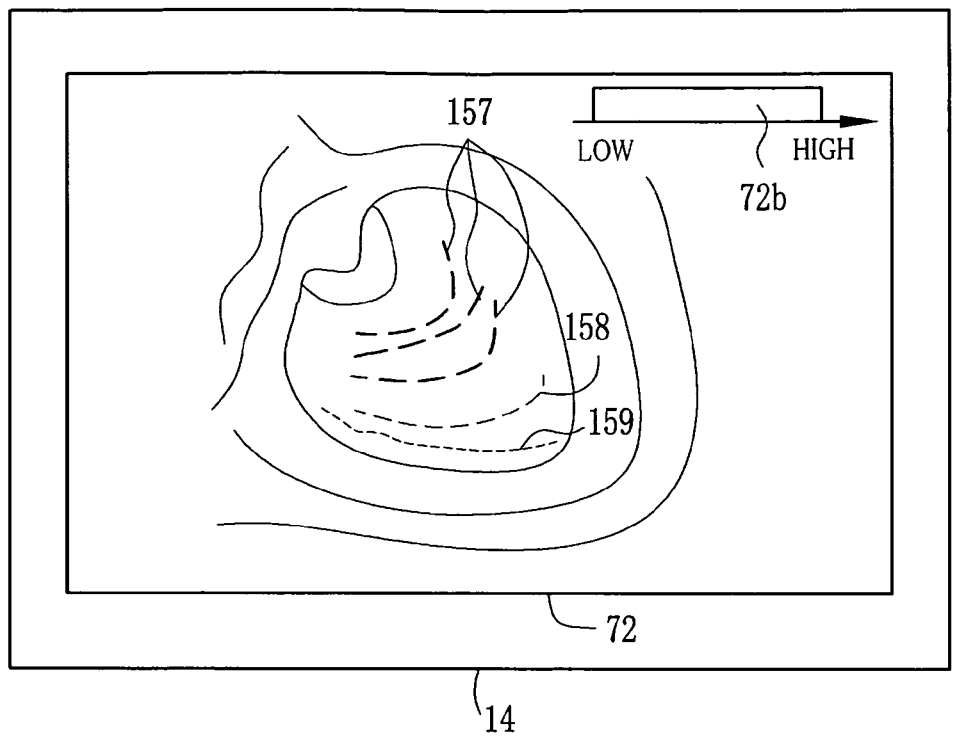
FIG. 33 is a diagram illustrating an example of an image displayed on a monitor, wherein superficial blood vessels are emphasized.

In the embodiment shown in FIG. 33, the vascular images 157 of a designated depth range are identified in the broadband light image 72. However, vascular images of a designated depth range may be identified in a vessel depth image 73, to reflect the color information about the oxygen saturation on the identified vascular images in the vessel depth image 73.

Moreover, in the embodiment shown in FIG. 33, it is possible to reduce the contrast of other vascular images 158 and 159 than the vascular images 157 that reflects the color information, in order that the vascular images 157 reflecting the color information will be more conspicuous.

Figure 34:
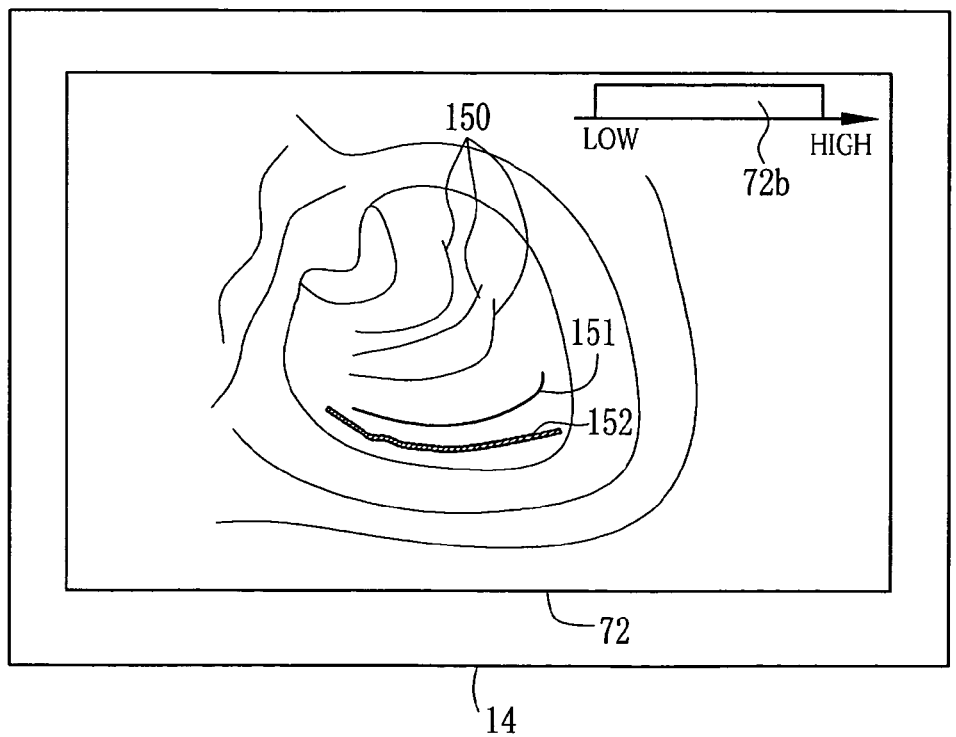
FIG. 34 is an explanatory diagram illustrating an embodiment, wherein color information indicating the oxygen saturation is reflected on those vessels having a given thickness or being in a given thickness range.

According to a further embodiment of the present invention, the thickness or diameter of every blood vessel contained in the broadband light image 72 is detected, and only those vessels having a given thickness or being in a given thickness range are sorted out to display color information about the oxygen saturation on these vessels. In order to detect the thickness of each vessel contained in the broadband light image 72, an electronic endoscope system of this embodiment should have a vessel thickness calculator (not shown) in a blood vessel image producer 57. In an example shown in FIG. 34, the vessel thickness calculator detects vessels 150 of small thickness, a vessel 151 of standard thickness, and a vessel 152 of large thickness. Then, color information about the oxygen saturation is reflected merely on the vessel 152 of large thickness. The color information may have the same pattern as any of the above embodiments. For example, cyan represents low oxygen saturation, and red represents high oxygen saturation. The broadband light image 72 also includes a color bar 72b showing the relation between the oxygen saturation and the color information. The color information about the oxygen saturation may be reflected not only on thick vessels but on fine vessels or vessels of standard thickness. Instead of the color information, gradation of a single color may be used as information about the oxygen saturation. It is also possible to design that three kinds of vascular information, i.e. the vessel thickness, the blood vessel depth and the oxygen saturation, may be reflected on individual vessels in the broadband light image.

Figure 35:
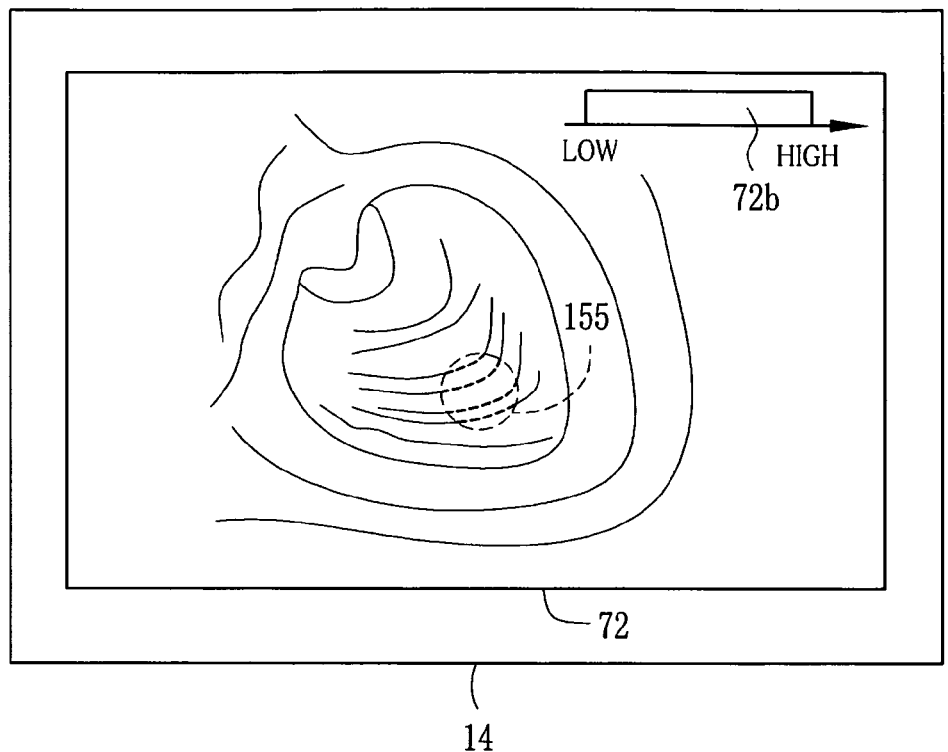
FIG. 35 is an explanatory diagram illustrating an embodiment, wherein color information indicating the oxygen saturation is reflected on those vessels which exist in an area where the density of blood vessels is at a given level or in a given range.

FIG. 35 shows another embodiment of the present invention, wherein density distribution of blood vessels in the body cavity is measured from a broadband light image 72, and then an area 155 of a given vessel density or in a given vessel density range is detected from the broadband light image 72. Color information corresponding to the oxygen saturation is reflected on only those vessels inside the area 155. In an electronic endoscope system of this embodiment, the blood vessel image producer 57 should include a vessel density calculator (not shown) for determining the density of the vessels in the broadband light image 72. Any of the above described color information patterns are applicable to this embodiment. Instead of the color information, gradation of a single color may be used as information about the oxygen saturation. It is also possible to configure that three kinds of vascular information, i.e. the vessel density, the blood vessel depth and the oxygen saturation, may be reflected on the vascular images.

Figure 36:
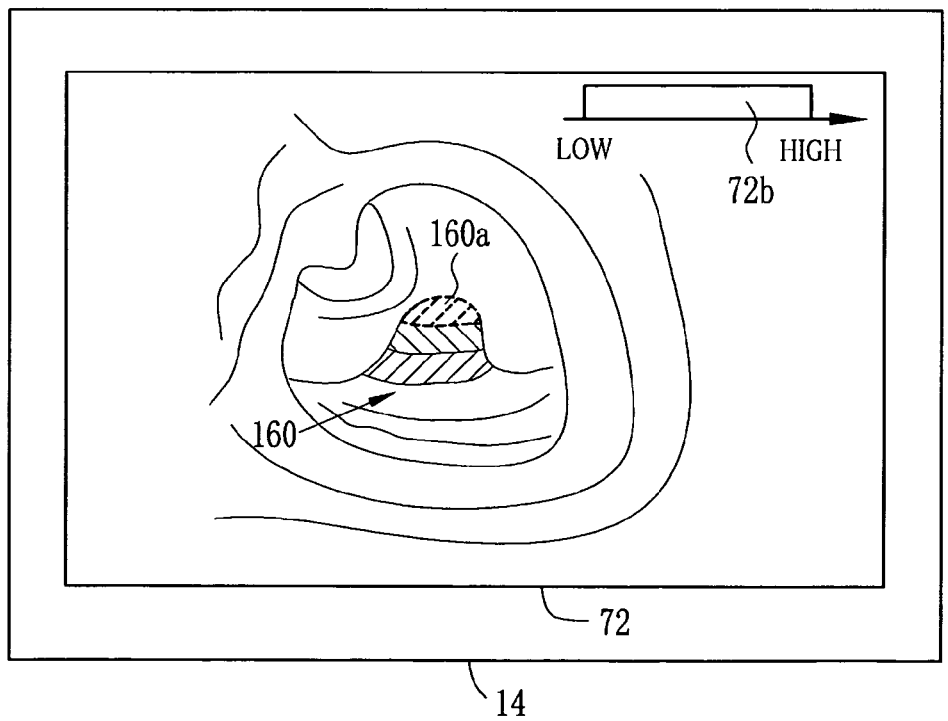
FIG. 36 is an explanatory diagram illustrating an embodiment, wherein color information indicating the oxygen saturation is reflected on those vessels which exist in an area where the fluorescence intensity of a fluorescent agent is at a given level or in a given range.

In a case where a 160 emits fluorescent light as being doped with a fluorescent agent, it is possible to measure the intensity distribution of the fluorescent light in a broadband light image 72. Thereafter, as shown in FIG. 36, an area 160a having a certain fluorescence intensity or in a certain fluorescence intensity range is detected from the broadband light image 72. Then, color information about the oxygen saturation is reflected only those vessels inside the detected area 160a. In an electronic endoscope system of this embodiment, the blood vessel image producer 57 should include a fluorescence intensity calculator (not shown) for determining the fluorescence intensity of the vessels in the broadband light image 72. Any of the above described color information patterns are applicable to this embodiment. Instead of the color information, gradation of a single color may be used as information about the oxygen saturation. It is also possible to configure that three kinds of vascular information, i.e. the fluorescence intensity, the blood vessel depth and the oxygen saturation, may be reflected on individual vessels in the broadband light image.

Figure 37:
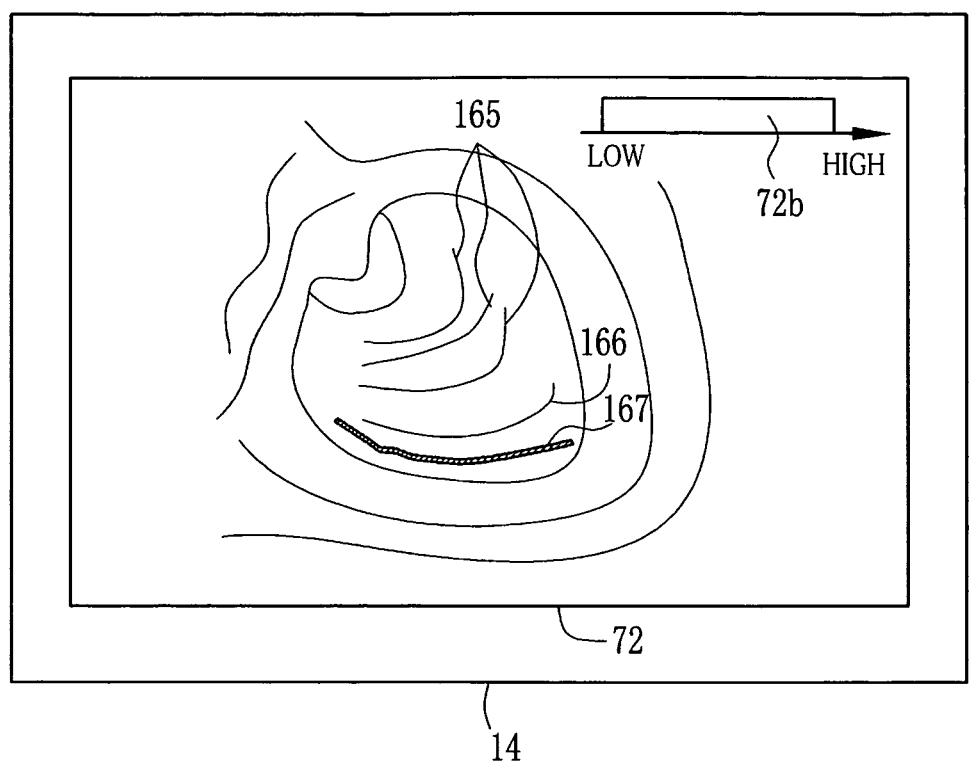
FIG. 37 is an explanatory diagram illustrating an embodiment, wherein color information indicating the oxygen saturation is reflected on those vessels having a given blood density or being in a given blood density range.

In another embodiment of the present invention, as shown in FIG. 37, blood concentration (hemoglobin index) of individual vessels 165, 166 and 167 is detected from the broadband light image 72. Based on the detected blood concentration, color information about the oxygen saturation is reflected on those vessels 167 having a certain blood concentration level or in a certain blood concentration range. In an electronic endoscope system of this embodiment, the blood vessel image producer 57 should include a blood concentration calculator (not shown) for detecting the blood concentration of the vessels in the broadband light image 72. Any of the above described color information is applicable to this embodiment. Instead of the color information, gradation of a single color may be used as information about the oxygen saturation. It is also possible to configure that three kinds of vascular information, i.e. the blood concentration, the blood vessel depth and the oxygen saturation, may be reflected on individual vessels in the broadband light image.

As a variation of the present invention, it is possible to determine the form of blood vessels, such as the number of branches, based on the broadband light image 72, so that color information about the oxygen saturation is reflected on those vessels having a specified form, e.g. vessels having a greater number of branches than a given value. In an electronic endoscope system of this embodiment, the blood vessel image producer 57 should include a vessel form calculator (not shown) for determining the formation of the vessels in the broadband light image 72. Any of the above described color information is applicable to this embodiment. Instead of the color information, gradation of a single color may be used as information about the oxygen saturation. It is also possible to configure that three kinds of vascular information, i.e. the form, the depth and the oxygen saturation of the blood vessels, may be reflected on individual vessels in the broadband light image.

In any of the above embodiments, the CCD 44 having RGB pixels may be replaced with a CCD that has a first kind of pixels provided with band-pass filters for passing the first narrowband ray N1 only, a second kind of pixels provided with band-pass filters for passing the second narrowband ray N2 only, and a third kind of pixels provided with band-pass filters for passing the third narrowband ray N3 only. With the CCD having the three kinds of band-pass filters, it comes to be possible to obtain information about the blood vessel depth and information about the oxygen saturation as well from an image frame that is captured under the broadband light BB. In conclusion, beside the above described methods, there may be a variety of other methods for obtaining information about the blood vessel depth and the oxygen saturation, and any method is applicable to the present invention, insofar as it is useful for measuring the blood vessel depth and the oxygen saturation.

Note that the present invention is applicable not only to the above-described electronic endoscope having the probing portion to be inserted into the body cavity, but also to a capsule-type electronic endoscope, wherein an image sensor, such as CCD, and other components are assembled into a capsule.

It should be understood that the present invention is not to be limited to the above embodiments, but many variations and modifications of the present invention will be possible for those skilled in the art without departing from the scope of the present invention as specified in the appended claims.

What is claimed is:

1. An electronic endoscope system comprising:
an illuminating device for projecting illumination light toward subject tissues inside a body cavity that include blood vessels, said illumination light including first to third narrowband rays, or having a wavelength range including all of the wavelength ranges of the first to third narrowband rays, at least one of the first and second narrowband rays having a central wavelength of not more than 450 nm, each of the first and second narrowband rays including such wavelengths, at which light absorbance in oxygenated hemoglobin differs from light absorbance in reduced hemoglobin that is not combined with oxygen, and the third narrowband rays having a wavelength range different from those of the first and second narrowband rays;
an electronic endoscope having an imaging device for capturing and outputting image signals that represent luminance of said illumination light as being projected toward and then reflected from said subject tissues;
a narrowband signal obtaining device for obtaining first to third narrowband signals from said image signals, the first to third narrowband signals corresponding to the first to third narrowband rays respectively;

a luminance ratio calculator for calculating a first luminance ratio between the first and third narrowband signals and a second luminance ratio between the second and third narrowband signals;

a first storage device previously storing correlations between the first and second luminance ratios and the vessel depth and the oxygen saturation; and a vascular information acquiring device for acquiring vascular information including both information about vessel depth and information about oxygen saturation representative of the percentage of oxygenated hemoglobin in the blood vessels based on the first and second luminance ratios calculated by said luminance ratio calculator by referring to the correlations stored in said first storage device.

2. The electronic endoscope system as claimed in claim 1, wherein the first storage device stores said correlations by correlating a luminance coordinate system that indicates the first and second luminance ratios to a vascular information coordinate system that indicates the information about vessel depth and the information about oxygen saturation;

said vascular information acquiring device determines first coordinates in said luminance coordinate system, corresponding to the first and second luminance ratios calculated by said luminance ratio calculator, and then determines second coordinates in said vascular information coordinate system, corresponding to the first coordinates of said luminance coordinate system, one coordinate value of the second coordinates representing the information about vessel depth and the other coordinate value of the second coordinates representing the information about oxygen saturation.

3. The electronic endoscope system as claimed in claim 1, wherein the first narrowband rays have a wavelength range of 440±10 nm, the second narrowband rays have a wavelength range of 470±10 nm, and the third narrowband ray has a wavelength range of 400±10 nm.

4. The electronic endoscope system as claimed in claim 1, wherein said imaging device has red pixels, green pixels and blue pixels, which are provided with red, green and blue filters respectively, and said illuminating device is capable of projecting white broadband light having a wavelength range covering red, green and blue regions, to which the red, green and blue pixels are respectively sensitive, wherein said electronic endoscope system further comprises an ordinary image producer for producing an ordinary image from said image signals as captured while the white broadband light is being projected.

5. The electronic endoscope system as claimed in claim 4, wherein two of the first to third narrowband rays have wavelength ranges, to which either the blue pixel or the green pixel is sensitive, whereas a remaining one of the first to third narrowband rays has a wavelength range, to which both the blue pixel and the green pixel are sensitive.

6. The electronic endoscope system as claimed in claim 5, wherein said illuminating device is capable of projecting the first to third narrowband rays individually, and wherein said narrowband signal obtaining device obtains the first to third narrowband signal from first and second frames of said image signals, the first frame being captured while said illuminating device is projecting one of the first to third narrowband rays that has a wavelength range, to which either the blue pixel or the green pixel is sensitive, the second frame being captured while said illuminating device is projecting other two of the first to third narrowband rays simultaneously.

7. The electronic endoscope system as claimed in claim 5, further comprising a second storage device storing correlation between luminance values of blue and green pixels contained in a frame of said image signals, which is captured under the white broadband light, wherein said illuminating device is capable of projecting the white broadband light and at least one of the first to third narrowband rays simultaneously;

said imaging device captures a first frame while said illuminating device is projecting one of the first to third narrowband rays that has a wavelength range, to which either the blue pixel or the green pixel is sensitive, simultaneously with the white broadband light, and said imaging device captures a second frame while said illuminating device is projecting other two of the first to third narrowband rays simultaneously with the white broadband light; and said narrowband signal obtaining device obtains the first to third narrowband signals by subtracting those luminance values which are based on the white broadband light from respective luminance values of the first and second frames, with reference to the correlation stored in the second storage device.

8. The electronic endoscope system as claimed in claim 1, wherein said illuminating device is capable of projecting the first to third narrowband rays individually, and wherein said narrowband signal obtaining device obtains the first to third narrowband signals respectively from three frames of said image signals, which are captured respectively under the first to third narrowband rays which are sequentially projected from said illuminating device.

9. The electronic endoscope system as claimed in claim 1, wherein said illuminating device is capable of projecting white broadband light having a wavelength range covering from blue region to red region as well as all the wavelength ranges of the first to third narrowband rays, and wherein said electronic endoscope system further comprises an optical filter for filtering the white broadband light as reflected from the subject tissues, said optical filter being able to selectively pass one of the first to third narrowband rays therethrough to said imaging device, so said imaging device sequentially outputs image signals each corresponding to the one of the first to third narrowband rays that passes through said optical filter, and said narrowband signal obtaining device obtains these image signals as the first to third narrowband signals.

10. The electronic endoscope system as claimed in claim 1, further comprising a third narrowband signal obtaining device for obtaining a fourth narrowband signal corresponding to a fourth narrowband ray that has a different wavelength range from the first to third narrowband rays, wherein said vascular information acquiring device acquires the vascular information including information about both the vessel depth and the oxygen saturation on the basis of the first to fourth narrowband signals.

11. The electronic endoscope system as claimed in claim 1, further comprising a display device for displaying the information on the vessel depth and the information on the oxygen saturation selectively from one another or simultaneously with each other.

* * * * *